(12) United States Patent
Wood et al.

(10) Patent No.: US 6,465,645 B1
(45) Date of Patent: Oct. 15, 2002

(54) LONG CHAIN HINDERED AMINES AND COMPOSITIONS STABILIZED THEREWITH

(75) Inventors: Mervin G. Wood, Poughquag, NY (US); Andrea R. Smith, Wingdale, NY (US); James P. Galbo, Wingdale, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/836,100

(22) Filed: Apr. 17, 2001

(51) Int. Cl.$^7$ .................... C07D 251/54; A01N 25/08
(52) U.S. Cl. .................. 544/198; 544/209; 544/217; 544/218; 252/100
(58) Field of Search .................. 544/198, 209, 544/217, 218

(56) References Cited

U.S. PATENT DOCUMENTS

| | | | |
|---|---|---|---|
| 3,530,084 A | 9/1970 | Potts | 260/28.5 |
| 4,021,432 A | 5/1977 | Holt et al. | 260/293.64 |
| 4,046,737 A | 9/1977 | Holt et al. | 260/45.8 |
| 4,086,204 A | * 4/1978 | Cassandrini et al. | 544/182 |
| 4,141,883 A | 2/1979 | Soma et al. | 260/45.8 |
| 4,198,334 A | 4/1980 | Rasberger | 260/45.8 |
| 4,308,362 A | 12/1981 | Wiezer et al. | 525/328 |
| 4,319,030 A | 3/1982 | Wiezer et al. | 546/19 |
| 4,376,836 A | 3/1983 | Wiezer et al. | 524/100 |
| 4,379,721 A | 4/1983 | Qualitz et al. | 106/21 |
| 4,471,417 A | 9/1984 | Wiezer et al. | 544/113 |
| 4,496,649 A | 1/1985 | Leppard et al. | 430/372 |
| 4,504,661 A | * 3/1985 | Wiezer et al. | 544/198 |
| 4,533,688 A | 8/1985 | Toda et al. | 524/100 |
| 4,616,051 A | 10/1986 | Paolino | 524/102 |
| RE33,489 E | * 12/1990 | Berner et al. | 546/20 |
| 4,986,932 A | 1/1991 | Disteldorf et al. | 252/403 |
| 5,204,473 A | 4/1993 | Winter et al. | 546/188 |
| 5,679,794 A | * 10/1997 | Suhadolnik et al. | 546/186 |
| 5,879,694 A | 3/1999 | Morrison et al. | 424/405 |
| 5,964,905 A | 10/1999 | Camp et al. | 44/275 |

FOREIGN PATENT DOCUMENTS

| | | |
|---|---|---|
| EP | 0005922 | 12/1979 |
| EP | 0133964 | 3/1985 |
| EP | 0300160 | 1/1989 |
| EP | 0359488 | 3/1990 |
| JP | 57137358 | 8/1982 |
| JP | 3278554 | 12/1991 |
| JP | 11263884 | 9/1999 |
| WO | 94/13736 | 6/1994 |
| WO | WO-99 00450 A1 * | 1/1999 |
| WO | 00/22037 | 4/2000 |

OTHER PUBLICATIONS

Ullmann's Encyclopedia of Industrial Chemistry, vol. A5, pp. 29–30.
F. A. Ballentine et al., Inhibiting Color Fading of Dyed Candles with Cyasorb® Light Absorbers, NCA Technical Meeting, (1998).
Abstract for JP3278554 (1991).
Abstract for JP 57137358 (1982).
Abstract for JP 11263884 (1999).
Abstract for EP 0300160 (1989).

* cited by examiner

Primary Examiner—Mukund J. Shah
Assistant Examiner—Venkataraman Balasubrasubramanian
(74) Attorney, Agent, or Firm—Tyler A. Stevenson; Luther A. R. Hall

(57) ABSTRACT

Hindered amine compounds which are substituted by a long hydrocarbon chain are useful in a number of applications where the solubility or compatibility afforded by said substitution is needed. This is seen particularly for example with white, dyed, dipped, unscented and/or scented candle wax which is effectively stabilized against discoloration and fading by the incorporation therein of a long chain hindered amine alone or in combination with a UV absorber and/or an antioxidant.

7 Claims, No Drawings

LONG CHAIN HINDERED AMINES AND COMPOSITIONS STABILIZED THEREWITH

This invention pertains to hindered amine compounds which are substituted by a long hydrocarbon chain and which are useful in a number of applications where the solubility or compatibility afforded by said substitution is needed. This is seen particularly for example with white, dyed, dipped, unscented and/or scented candle wax which is effectively stabilized against discoloration and fading by the incorporation therein of a long chain hindered amine alone or in combination with a UV absorber and/or an antioxidant.

BACKGROUND OF THE INVENTION

Candles have been known for many centuries going back to the eighth century B.C. The nature of candles is described in Ullmann's Encyclopedia of Industrial Chemistry, Volume A5 at pages 29–30 where it is seen that candles are made from paraffin, beeswax and stearin as basic materials, and where a host of additives may also be present.

It is not surprising that with candles and wax becoming increasingly more important attention was paid as to how to stabilize the said materials. At the National Candle Association Meeting in Houston, 1994, R. van der Vennet presented a paper on "Antioxidants in Wax—Replacement of BHT" touting the use of Vitamin E (tocopherol) as an antioxidant to prevent the yellowing of wax when oxidized. WO 94/13736 describes the same invention.

EP 359,488 A3 and EP 133,964 B1 describe stabilized waxes used in cosmetics where the waxes are the same or similar to those used in candles.

EP 5,922 A1 describes lip cosmetics where the waxes are useful in lipsticks and are related to those useful in candles.

U.S. Pat. No. 5,879,694 describes in detail transparent gel candles both in composition and structure. The use of BHT as an antioxidant is mentioned.

At the National Candle Association Technical Meeting on Apr. 16, 1998, F. A. Ballentine et al., presented a paper entitled "Inhibiting Color Fading of Dyed Candles with CYASORB® Light Absorbers" in which the general theories of thermal oxidation and photodegradation are discussed along with data on the effect of light absorbers on color stability of dyed candle waxes. The light absorbers compared are 4-octyloxy-2-hydroxybenzophenone UV-531; 4-methoxy-2-hydroxybenzophenone UV-9; 2-(2-hydroxy-5-methylphenyl)-2H-benzotriazole UV-5365; 2-(2-hydroxy-5-tert-octylphenyl-2H-benzotriazole UV-5411 and 2-(2-hydroxy-3,5-di-tert-amylphenyl)-2H-benzotriazole UV-2337).

U.S. Pat. No. 5,964,905 teaches dyed and scented candle gels containing triblock copolymers and a hydrocarbon oil of high flash point. This reference teaches that a light (UV) absorber may be used to improve the shelf stability of the candle color when exposed to visible or ultraviolet light. Two preferred absorbers are ethylhexyl p-methoxycinnamate (PARSOL® MCX, Roche) and 2-(2-hydroxy-5-tert-octylphenyl)-2H-benzotriazole (CYASORB® 5411, Cytec).

WO 00/22037 teaches the stabilization of solid, shaped and colored wax articles, including candles, using a malonate UV absorber which may optionally contain a hindered amine moiety as part of the malonate compound structure. The wax articles are dyed with a variety of oil soluble dyes and pigments. The samples protected by dimethyl p-methoxy-benzylidinemalonate exhibited better resistance to discoloration that did samples stabilized with selected benzotriazole or benzophenone UV absorbers.

Japanese Hei 3-278554 teaches that wax crayons (drawing materials) colored by organic pigments can be stabilized by a hindered amine and/or benzotriazole.

In respect to wax stabilization, the use of selected hindered amines and/or benzotriazole UV absorbers is also known in the prior art as seen in U.S. Pat. Nos. 3,530,084; 4,379,721; 4,616,051 and 5,964,905 and copending applications Ser. Nos. 09/495,495, 09/495,496 and 09/741,583.

U.S. Pat. Nos. 4,046,737; 4,021,432 and 4,049,647 teach piperidine derivatives having substituted by alkyl, alkenyl or alkynyl groups of 1 to 20 carbon atoms.

Japanese Sho 57-137,358 describes piperidine derivatives substituted on the N-atom by a group containing a polymerizable double bond.

EP 300,160 and Japanese Hei 11-263,884 depict piperidine dervatives substituted on the 4-position by a monocarboxylic acid of 16 to 24 carbon atoms. The resulting hindered amine is useful for stabilizing lubricating oils, cosmetics and polyolefins.

U.S. Pat. No. 4,376,836 disclose triazylaminotriazines substituted by hindered piperidine groups where the longest chain in said molecules contain 18 carbon atoms. These molecules are used to stabilize polyolefins.

U.S. Pat. No. 4,319,030 teaches alkylated diazaspirodecanes which may contain alkyl groups of 1 to 30 carbon atoms. These compounds are used as stabilizers for polyolefins.

U.S. Pat. No. 4,986,932 describes polyolefin compositions containing a benzotriazole or benzophenone UV absorber and a hindered piperidine substituted on the 4-position by a ester group containing 16–24 carbon atoms.

U.S. Pat. No. 4,308,362 discloses copolymers of polymerizable hindered piperidine derivatives which are useful for the stabilization of polyolefins.

U.S. Pat. No. 4,198,334 teaches substituted malonic acid derivatives containing hindered piperidine derivatives which may be substituted with alkyl groups of 1 to 20 carbon atoms.

U.S. Pat. No. 4,496,649 describes color photographic recording material containing hindered piperidine derivatives, but containing aromatic moieties in the molecules.

U.S. Pat. No. 4,141,883 discloses 2,2,6,6-tetraalkylpiperidine compounds substituted on the 4-position by an alkyloxy or acyloxy group of 1 to 18 carbon atoms. These materials are useful for stabilizing polyolefins.

U.S. Pat. No. 4,471,417 teaches poly-bis-triazinylimides which contain hindered amine piperidine moieties and alkyl groups of 1 to 18 carbon atoms. These compounds are useful for stabilizing polyolefins.

U.S. Pat. No. 4,533,688 discloses tris (piperidylaminotriazylamino) compounds which contain alkyl moieties of 1 to 18 carbon atoms. These compounds are useful for the stabilization of polyolefins U.S. Pat. No. 5,204,473 and copending application Ser. No. 09/257,711 describe hindered amine compounds related to the instant compounds, but without the long chain substitution.

None of these references teach the instant long chain hindered amine compounds themselves or the superior performance provided when said long chain hindered amine compounds are used alone or in conjunction with a UV absorber and/or antioxidant to stabilize candle wax and other compositions subject to degradation.

OBJECTS OF THE INVENTION

The object of the invention is to provide for hindered amine compounds substituted by a long chain hydrocarbon moiety.

Another object of the invention is to provide for a white and unscented; white and scented; dyed and unscented; dyed and scented; dipped and unscented; or dipped and scented candle wax stabilized by a long chain hindered amine or UV absorber compound alone or in combination with a UV absorber and/or antioxidant.

Still another object of the invention is thermoplastic resin compositions stabilized with the instant hindered amines, particularly polyolefins and polyesters.

DETAILED DISCLOSURE

The instant invention pertains to a compound of formula 1 to 6

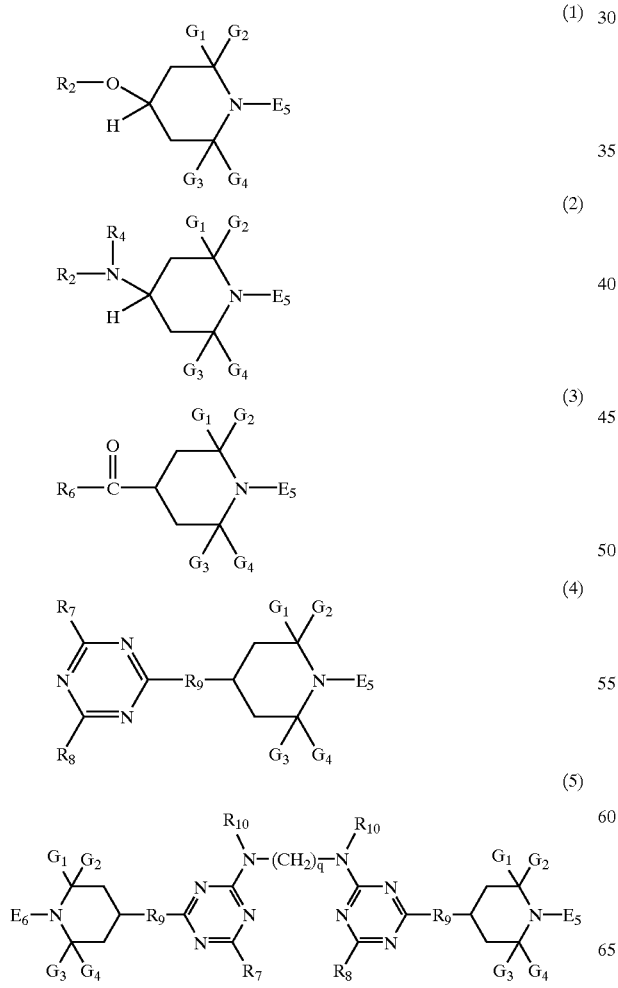

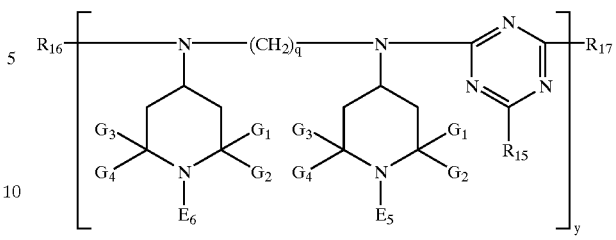

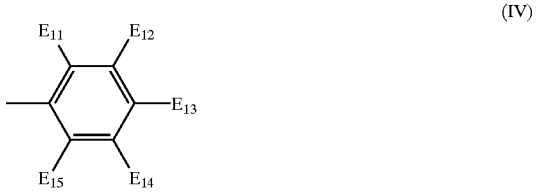

$G_1$, $G_2$, $G_3$, and $G_4$ are independently alkyl of 1 to 8 carbon atoms, or $G_1$ and $G_2$ together are pentamethylene, or $G_3$ and $G_4$ together are pentamethylene;

$E_5$ is $OE_9$ or $-O-E-(OH)_b$;

$E_9$ is straight or branched chain alkyl of 1 to 24 carbon atoms, cycloalkyl of 5 to 12 carbon atoms, straight or branched chain alkenyl of 3 to 24 carbon atoms, cycloalkenyl of 5 to 12 carbon atoms, phenylalkyl of 7 to 15 carbon atoms, a radical of a saturated or unsaturated bicyclic or tricyclic hydrocarbon of 7 to 15 carbon atoms, aryl of 6 to 10 carbon atoms or said aryl substituted by one to three alkyl of 1 to 4 carbon atoms; or a group of formula IV (IV)

$E_{11}$ to $E_{15}$ are independently hydrogen, halogen, nitro, cyano, alkyl of 1 to 18 carbon atoms, phenylalkyl of 7 to 15 carbon atoms, aryl of 6 to 10 carbon atoms, hydroxyl, carboxyl, alkylthio of 1 to 18 carbon atoms, alkoxy or 1 to 18 carbon atoms, phenylalkoxy of 7 to 15 carbon atoms, aryloxy of 6 to 10 carbon atoms, alkylcarbonyloxy of 2 to 18 carbon atoms, alkylsulfonyl of 1 to 18 carbon atoms, arylsulfonyl of 6 to 15 carbon atoms, sulfo or phosphono, or any two vicinal substituents connected together to form a mono- or polycyclic ring;

E is a straight or branched chain alkylene of 1 to 18 carbon atoms, cycloalkylene of 5 to 18 carbon atoms, cycloalkenylene of 5 to 18 carbon atoms, a straight or branched chain alkylene of 1 to 4 carbon atoms substituted by phenyl or by phenyl substituted by one or two alkyl groups of 1 to 4 carbon atoms;

b is 1, 2 or 3 with the proviso that b cannot exceed the number of carbon atoms in E, and when b is 2 or 3, each hydroxyl group is attached to a different carbon atom of E;

$R_2$ is $T_1$, $-CO-T_1$, $-CO-X-T_1$, $-(CH_2)_m-CO-X-T_1$, $-(CH_2)_p-X-CO-T_1$, $-CO-(CH_2)_m-CO-X-T_1$, or $-CO-(CH_2)_p-X-CO-T_1$;

m is 1 to 12;

p is 1 to 12;

$T_1$ is straight or branched chain alkyl of 19 to 100 carbon atoms, or said alkyl substituted by one hydroxyl group and interrupted by one oxa moiety, or a mixture of such alkyl moieties; or $T_1$, is —(R—O)$_n$—R—OG$_5$ where R is ethylene, propylene, trimethylene, 1,2-butylene or tetramethylene, and n is 4 to 49 so that the total number of carbon atoms in $T_1$ is at least 20;

$G_5$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms;

X and $X_1$ are independently —O—, or —N—($R_4$)—;

$R_4$ is hydrogen, alkyl of 1 to 18 carbon atoms or acyl of 2 to 6 carbon atoms;

$R_6$ is $T_1$, —X—$T_1$, —(CH$_2$)$_m$—CO—X—$T_1$, —(CH$_2$)$_p$—X—CO—$T_1$, X—(CH$_2$)$_m$—CO—X—$T_1$, or X—(CH$_2$)$_p$—X$_1$—CO—$T_1$;

$R_7$ and $R_8$ are independently chlorine, alkoxy of 1 to 18 carbon atoms, —O—$T_2$, amino substituted by 2-hydroxyethyl, —NH(alkyl) of 1 to 18 carbon atoms, —N(alkyl)$T_2$ with alkyl of 1 to 18 carbon atoms, —N(alkyl)$_2$ of 2 to 36 carbon atoms, —X—$T_1$, X—(CH$_2$)$_m$—CO—X$_1$—$T_1$, or X—(CH$_2$)$_p$—X$_1$—CO—$T_1$;

$R_9$ is a divalent oxygen atom, or $R_9$ is a divalent nitrogen atom substituted by either hydrogen, alkyl of 1 to 12 carbon atoms or $T_2$

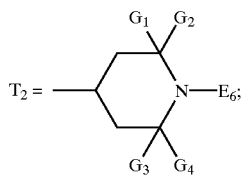

$E_6$ is hydrogen, oxyl, hydroxyl, straight or branched chain alkyl of 1 to 24 carbon atoms, straight or branched chain alkenyl of 3 to 24 carbon atoms, benzyl, acetyl, —CH$_2$CH(OH)—$E_8$, —OE$_9$, or, —OE(OH)$_b$;

$E_8$ is hydrogen, methyl, ethyl or phenyl;

$R_{10}$ is hydrogen or an alkyl group of 1 to 18 carbon atoms;

q is 2 to 8;

y is 1 to 10;

$R_{15}$ is morpholino, piperidino, 1-piperizinyl, alkylamino of 1 to 18 carbon atoms, especially branched alkylamino of 3 to 8 carbon atoms such as tert-octylamino, —N(alkyl)$T_2$ with alkyl of 1 to 8 carbon atoms, —N(alkyl)$_2$ of 2 to 16 carbon atoms, —X—$T_1$, X—(CH$_2$)$_m$—CO—X$_1$—$T_1$, or X—(CH$_2$)$_p$—X$_1$—CO—$T_1$;

$R_{16}$ is hydrogen, acyl of 2 to 4 carbon atoms, carbamoyl substituted by alkyl of 1 to 4 carbon atoms, s-triazinyl substituted once by chlorine and once by $R_{15}$, or s-triazinyl substituted twice by $R_{15}$ with the condition that the two $R_{15}$ substituents may be different;

$R_{17}$ is chlorine, amino substituted by alkyl of 1 to 18 carbon atoms or by $T_2$, —N(alkyl)$T_2$ with alkyl of 1 to 8 carbon atoms, —N(alkyl)$_2$ of 2 to 16 carbon atoms, or the group $T_3$

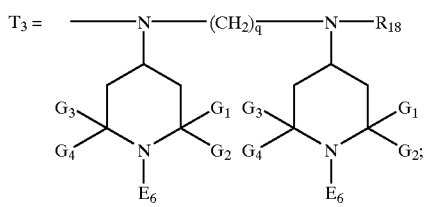

$R_{18}$ is hydrogen, acyl of 2 to 4 carbon atoms, carbamoyl substituted by alkyl of 1 to 4 carbon atoms, s-triazinyl substituted twice by —N(alkyl)$_2$ of 2 to 16 carbon atoms or s-triazinyl substituted twice by —N(alkyl)$T_1$ with alkyl of 1 to 8 carbon atoms;

with the proviso that at least one of $R_2$, $R_6$, $R_7$, $R_8$, or $R_{15}$ is a group which contains a $T_1$ moiety.

It is understood that whether $T_1$ is an alkyl group or a —(R—O)$_n$—R—OG$_5$ group that such moieties are usually a mixture of molecular weights falling within the scope of the total number of atoms indicated.

When R is ethylene, the group $T_1$ is —(CH$_2$CH$_2$O)$_n$—CH$_2$CH$_2$OG$_5$ where n is 9 to 49.

When R is propylene, the group $T_1$ is —(CH(CH$_3$)CH$_2$O)$_n$—CH(CH$_3$)CH$_2$OG$_5$ where n is 6 to 32.

When R is trimethylene, the group $T_1$ is —(CH$_2$CH$_2$CH$_2$O)$_n$—CH$_2$CH$_2$CH$_2$OG$_5$ where n is 6 to 32.

When R is tetramethylene, the group $T_1$ is —(CH$_2$CH$_2$CH$_2$CH$_2$O)$_n$—CH$_2$CH$_2$CH$_2$CH$_2$OG$_5$ where n is 4 to 24. Also R is also 1,2-butylene so that $T_1$ is —(CH(CH$_2$CH$_3$)CH$_2$O)$_n$—CH(CH$_2$CH$_3$)CH$_2$OG$_5$ where n is 4 to 24.

Other embodiments of formula (1) are

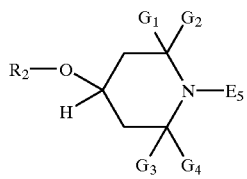

(1)

$G_1$, $G_2$, $G_3$, and $G_4$ are each methyl;

$E_5$ is OE$_9$ or —O—E—(OH)$_b$;

$E_9$ is straight or branched chain alkyl of 1 to 18 carbon atoms, cycloalkyl of 5 to 12 carbon atoms, straight or branched chain alkenyl of 3 to 24 carbon atoms, cycloalkenyl of 5 to 12 carbon atoms; or a group of formula IV

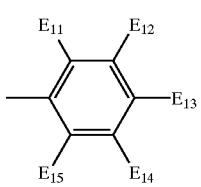

(IV)

$E_{11}$ to $E_{15}$ are independently hydrogen, F, Cl, Br, nitro, cyano, hydroxyl, carboxyl, alkylthio of 1 to 18 carbon atoms, or alkoxy or 1 to 18 carbon atoms;

when b is 1, E—OH is respectively a carbon-centered radical formed from 2-methyl-2-propanol, 2-propanol, 2,2-dimethyl-1-propanol, 2-methyl-2-butanol, ethanol, 1-propanol, 1-butanol, 1-pentanol, 1-hexanol, 1-nonanol, 1-decanol, 1-dodecanol, 1-octadecanol, 2-butanol, 2-pentanol, 2-ethyl-1-hexanol, cyclohexanol, cyclooctanol, allyl alcohol, phenethyl alcohol or 1-phenyl-1-ethanol;

when b is 2, E—OH is respectively a carbon-centered radical or diradical formed from 1,2-ethanediol, 1,2-propanediol, 1,3-propanediol, 1,2-butanediol, 1,3-butanediol, 1,4-butanediol, 2,2-dimethyl-1,3-propanediol, 1,2-cyclohexanediol, 1,3-cyclohexanediol or 1,4-cyclohexanediol; most preferably E—OH is formed from 1,4-butanediol, 2,2-dimethyl-1,3-propanediol, 1,2-cyclohexanediol, 1,3-cyclohexanediol or when b is 3, E—OH is respectively a carbon-centered radical formed from glycerol, 1,1,1-tris(hydroxymethyl)methane, 2-ethyl-2-(hydroxymethyl-1,3-propanediol, 1,2,4-butanetriol or 1,2,6-hexanetriol;

$R_2$ is —CO—$T_1$, —CO—X—$T_1$, (CH$_2$)$_m$—CO—X—$T_1$, or —(CH$_2$)$_p$—X—CO—$T_1$;

m is 1 to 4;

p is 1 to 4;

$T_1$ is straight or branched chain alkyl of 19 to 80 carbon atoms, or a mixture of such alkyl moieties; or $T_1$ is —(R—O)$_n$—R—OG$_5$ where R is ethylene, or propylene, and n is 6 to 49 so that the total number of carbon atoms in $T_1$ is at least 20;

$G_5$ is hydrogen, straight or branched chain alkyl of 1 to 24 carbon atoms;

X and $X_1$ are independently —O—, or —N—(R$_4$)—; and $R_4$ is hydrogen, alkyl of 1 to 18 carbon atoms or acyl of 2 to 6 carbon atoms.

Other embodiments of formula (2) are

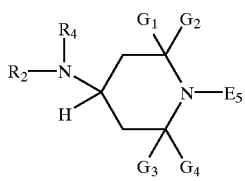

(2)

$G_1$, $G_2$, $G_3$, and $G_4$ are each methyl;

$E_5$ is OE$_9$ or —O—E—(OH)$_b$;

$E_9$ is straight or branched chain alkyl of 1 to 18 carbon atoms, cycloalkyl of 5 to 12 carbon atoms, straight or branched chain alkenyl of 3 to 24 carbon atoms, cycloalkenyl of 5 to 12 carbon atoms; or a group of formula IV

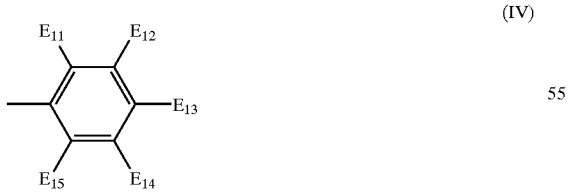

(IV)

$E_{11}$ to $E_{15}$ are independently hydrogen, F, Cl, Br, nitro, cyano, hydroxyl, carboxyl, alkylthio of 1 to 18 carbon atoms, or alkoxy or 1 to 18 carbon atoms;

when b is 1, E—OH is respectively a carbon-centered radical formed from 2-methyl-2-propanol, 2-propanol, 2,2-dimethyl-1-propanol, 2-methyl-2-butanol, ethanol, 1-propanol, 1-butanol, 1-pentanol, 1-hexanol, 1-nonanol, 1-decanol, 1-dodecanol, 1-octadecanol, 2-butanol, 2-pentanol, 2-ethyl-1-hexanol, cyclohexanol, cyclooctanol, allyl alcohol, phenethyl alcohol or 1-phenyl-1-ethanol;

when b is 2, E—OH is respectively a carbon-centered radical or diradical formed from 1,2-ethanediol, 1,2-propanediol, 1,3-propanediol, 1,2-butanediol, 1,3-butanediol, 1,4-butanediol, 2,2-dimethyl-1,3-propanediol, 1,2-cyclohexanediol, 1,3-cyclohexanediol or 1,4-cyclohexanediol;

when b is 3, E—OH is respectively a carbon-centered radical formed from glycerol, 1,1,1-tris(hydroxymethyl)methane, 2-ethyl-2-(hydroxymethyl-1,3-propanediol, 1,2,4-butanetriol or 1,2,6-hexanetriol;

$R_2$ is —O—$T_1$, —CO—X—$T_1$, —(CH$_2$)$_m$—CO—X—$T_1$, or —(CH$_2$)$_p$—X—CO—$T_1$;

m is 1 to 4;

p is 1 to 4;

$T_1$ is straight or branched chain alkyl of 19 to 80 carbon atoms, or a mixture of such alkyl moieties; or $T_1$ is —(R—O)$_n$—R—OG$_5$ where R is ethylene, or propylene, and n is 6 to 49 so that the total number of carbon atoms in $T_1$ is at least 20;

$G_5$ is hydrogen, straight or branched chain alkyl of 1 to 24 carbon atoms;

X and $X_1$ are independently —O—, or —N—(R$_4$)—; and $R_4$ is hydrogen, alkyl of 1 to 18 carbon atoms or acyl of 2 to 6 carbon atoms.

Other embodiments of formula (3) are

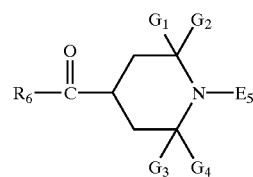

(3)

$G_1$, $G_2$, $G_3$, and $G_4$ are each methyl;

$E_5$ is OE$_9$ or —O—E—(OH)$_b$;

$E_9$ is straight or branched chain alkyl of 1 to 24 carbon atoms, cycloalkyl of 5 to 12 carbon atoms, straight or branched chain alkenyl of 3 to 24 carbon atoms, or cycloalkenyl of 5 to 12 carbon atoms; or a group of formula IV

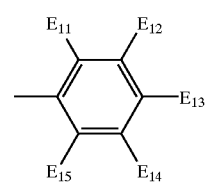

(IV)

$E_{11}$ to $E_{15}$ are independently hydrogen, F, Cl, Br, nitro, cyano, hydroxyl, carboxyl, alkylthio of 1 to 18 carbon atoms, or alkoxy or 1 to 18 carbon atoms;

when b is 1, E—OH is respectively a carbon-centered radical formed from 2-methyl-2-propanol, 2-propanol, 2,2-dimethyl-1-propanol, 2-methyl-2-butanol, ethanol, 1-propanol, 1-butanol, 1-pentanol, 1-hexanol, 1-nonanol, 1-decanol, 1-dodecanol, 1-octadecanol, 2-butanol, 2-pentanol, 2-ethyl-1-hexanol, cyclohexanol, cyclooctanol, allyl alcohol, phenethyl alcohol or 1-phenyl-1-ethanol;

when b is 2, E—OH is respectively a carbon-centered radical or diradical formed from 1,2-ethanediol, 1,2-propanediol, 1,3-propanediol, 1,2-butanediol, 1,3-butanediol, 1,4-butanediol, 2,2-dimethyl-1,3-propanediol, 1,2-cyclohexanediol, 1,3-cyclohexanediol or 1,4-cyclohexanediol;

when b is 3, E—OH is respectively a carbon-centered radical formed from glycerol, 1,1,1-tris(hydroxymethyl)methane, 2-ethyl-2-(hydroxymethyl-1,3-propanediol, 1,2,4-butanetriol or 1,2,6-hexanetriol;

m is 1 to 4;

p is 1 to 4;

$T_1$ is straight or branched chain alkyl of 19 to 80 carbon atoms, or a mixture of such alkyl moieties; or $T_1$ is —(R—O)$_n$—R—OG$_5$ where R is ethylene, or propylene, and n is 6 to 49 so that the total number of carbon atoms in $T_1$, is at least 20;

$G_5$ is hydrogen, or straight or branched chain alkyl of 1 to 24 carbon atoms;

X and $X_1$ are independently —O—, or —N—(R$_4$)—;

$R_4$ is hydrogen, alkyl of 1 to 18 carbon atoms or acyl of 2 to 6 carbon atoms; and $R_6$ is —X—$T_1$, X—(CH$_2$)$_m$—CO—X$_1$—$T_1$, or X—(CH$_2$)$_p$—X$_1$—CO—$T_1$.

Other embodiments of formula (4) are

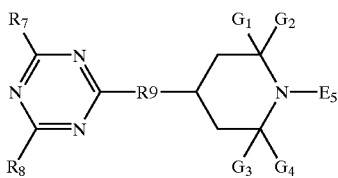

(4)

$G_1$, $G_2$, $G_3$, and $G_4$ are each methyl;

$E_5$ is OE$_9$ or —O—E—(OH)$_b$;

$E_9$ is straight or branched chain alkyl of 1 to 24 carbon atoms, cycloalkyl of 5 to 12 carbon atoms, straight or branched chain alkenyl of 3 to 24 carbon atoms, or cycloalkenyl of 5 to 12 carbon atoms; or a group of formula IV

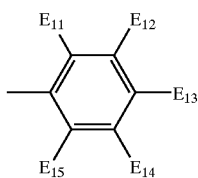

(IV)

$E_{11}$ to $E_{15}$ are independently hydrogen, F, Cl, Br, nitro, cyano, hydroxyl, carboxyl, alkylthio of 1 to 18 carbon atoms, alkoxy or 1 to 18 carbon atoms;

when b is 1, E—OH is respectively a carbon-centered radical formed from 2-methyl-2-propanol, 2-propanol, 2,2-dimethyl-1-propanol, 2-methyl-2-butanol, ethanol, 1-propanol, 1-butanol, 1-pentanol, 1-hexanol, 1-nonanol, 1-decanol, 1-dodecanol, 1-octadecanol, 2-butanol, 2-pentanol, 2-ethyl-1-hexanol, cyclohexanol, cyclooctanol, allyl alcohol, phenethyl alcohol or 1-phenyl-1-ethanol;

when b is 2, E—OH is respectively a carbon-centered radical or diradical formed from 1,2-ethanediol, 1,2-propanediol, 1,3-propanediol, 1,2-butanediol, 1,3-butanediol, 1,4-butanediol, 2,2-dimethyl-1,3-propanediol, 1,2-cyclohexanediol, 1,3-cyclohexanediol or 1,4-cyclohexanediol;

when b is 3, E—OH is respectively a carbon-centered radical formed from glycerol, 1,1,1-tris(hydroxymethyl)methane, 2-ethyl-2-hydroxymethyl-1,3-propanediol, 1,2,4-butanetriol or 1,2,6-hexanetriol;

m is 1 to 4;

p is 1 to 4;

$T_1$ is straight or branched chain alkyl of 19 to 80 carbon atoms, or a mixture of such alkyl moieties; or $T_1$ is —(R—O)$_n$—R—OG$_5$ where R is ethylene, or propylene and n is 4 to 49 so that the total number of carbon atoms in $T_1$ is at least 20;

$G_5$ is hydrogen, straight or branched chain alkyl of 1 to 24 carbon atoms;

X and $X_1$ are independently —O—, or —N—(R$_4$)—;

$R_4$ is hydrogen, alkyl of 1 to 18 carbon atoms or acyl of 2 to 6 carbon atoms;

$R_7$ and $R_8$ are independently alkoxy of 1 to 18 carbon atoms, —O—$T_2$, amino substituted by 2-hydroxyethyl, —N(alkyl)$T_2$ with alkyl of 1 to 18 carbon atoms, —X—$T_1$, X—(CH$_2$)$_m$—CO—X$_1$—$T_1$, or X—(CH$_2$)$_p$—X$_1$—CO—$T_1$;

$R_9$ is a divalent oxygen atom, or $R_9$ is a divalent nitrogen atom substituted by either hydrogen, alkyl of 1 to 12 carbon atoms or $T_2$

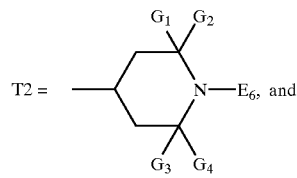

$E_6$ is hydrogen, hydroxyl, straight or branched chain alkyl of 1 to 24 carbon atoms, straight or branched chain alkenyl of 3 to 24 carbon atoms, benzyl, acetyl, —OE$_9$, or —OE(OH)$_b$.

Other embodiments of structure (5) are

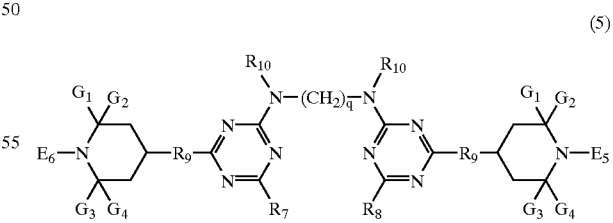

(5)

$G_1$, $G_2$, $G_3$, and $G_4$ are each methyl;

$E_5$ is OE$_9$ or —O—E—(OH)$_b$;

$E_9$ is straight or branched chain alkyl of 1 to 24 carbon atoms, cycloalkyl of 5 to 12 carbon atoms, straight or branched chain alkenyl of 3 to 24 carbon atoms, or cycloalkenyl of 5 to 12 carbon atoms; or a group of formula IV

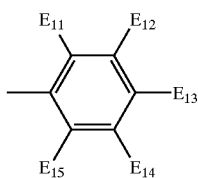

(IV)

$E_{11}$ to $E_{15}$ are independently hydrogen, F, Cl, Br, nitro, cyano, hydroxyl, carboxyl, alkylthio of 1 to 18 carbon atoms, or alkoxy or 1 to 18 carbon atoms;

when b is 1, E—OH is respectively a carbon-centered radical formed from 2-methyl-2-propanol, 2-propanol, 2,2-dimethyl-1-propanol, 2-methyl-2-butanol, ethanol, 1-propanol, 1-butanol, 1-pentanol, 1-hexanol, 1-nonanol, 1-decanol, 1-dodecanol, 1-octadecanol, 2-butanol, 2-pentanol, 2-ethyl-1-hexanol, cyclohexanol, cyclooctanol, allyl alcohol, phenethyl alcohol or 1-phenyl-1-ethanol;

when b is 2, E—OH is respectively a carbon-centered radical or diradical formed from 1,2-ethanediol, 1,2-propanediol, 1,3-propanediol, 1,2-butanediol, 1,3-butanediol, 1,4-butanediol, 2,2-dimethyl-1,3-propanediol, 1,2-cyclohexanediol, 1,3-cyclohexanediol or 1,4-cyclohexanediol;

when b is 3, E—OH is respectively a carbon-centered radical formed from glycerol, 1,1,1-tris(hydroxymethyl)methane, 2-ethyl-2-hydroxymethyl-1,3-propanediol, 1,2,4-butanetriol or 1,2,6-hexanetriol;

m is 1 to 4;

p is 1 to 4;

$T_1$ is straight or branched chain alkyl of 19 to 80 carbon atoms or a mixture of such alkyl moieties; or $T_1$ is —(R—O)$_n$—R—OG$_5$ where R is ethylene or propylene and n is 4 to 49 so that the total number of carbon atoms in $T_1$ is at least 20;

$G_5$ is hydrogen, straight or branched chain alkyl of 1 to 24 carbon atoms;

X and $X_1$ are independently —O—, or —N—($R_4$)—;

$R_4$ is hydrogen, alkyl of 1 to 18 carbon atoms;

$R_7$ and $R_8$ are independently alkoxy of 1 to 18 carbon atoms, -O-$T_2$, amino substituted by 2-hydroxyethyl, —NH(alkyl) of 1 to 18 carbon atoms, —N(alkyl)$T_2$ with alkyl of 1 to 18 carbon atoms, —X—$T_1$, X—(CH$_2$)$_m$—CO—$X_1$—$T_1$, or X—(CH$_2$)$_p$—$X_1$—CO—$T_1$;

$R_9$ is a divalent oxygen atom, or $R_9$ is a divalent nitrogen atom substituted by either hydrogen, alkyl of 1 to 12 carbon atoms or $T_2$

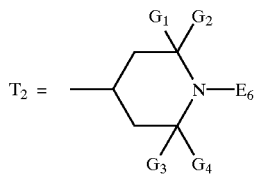

$E_6$ is hydrogen, oxyl, hydroxyl, straight or branched chain alkyl of 1 to 24 carbon atoms, straight or branched chain alkenyl of 3 to 24 carbon atoms, acetyl, —OE$_9$, or, —OE(OH)$_b$;

$R_{10}$ is hydrogen or an alkyl group of 1 to 18 carbon atoms; and q is 4 to 8.

Other embodiments of structure (6) are

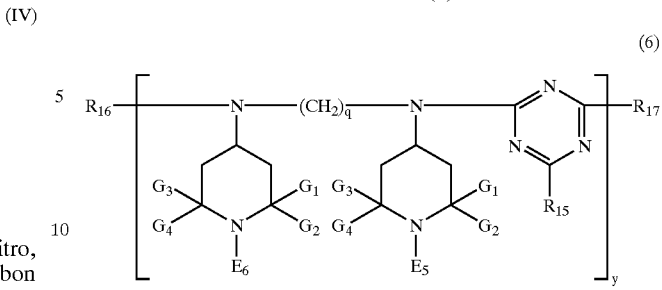

$G_1$, $G_2$, $G_3$, and $G_4$ are each methyl;

$E_5$ is OE$_9$ or —O—E—(OH)$_b$;

$E_9$ is straight or branched chain alkyl of 1 to 24 carbon atoms, cycloalkyl of 5 to 12 carbon atoms, straight or branched chain alkenyl of 3 to 24 carbon atoms, or cycloalkenyl of 5 to 12 carbon atoms; or a group of formula IV

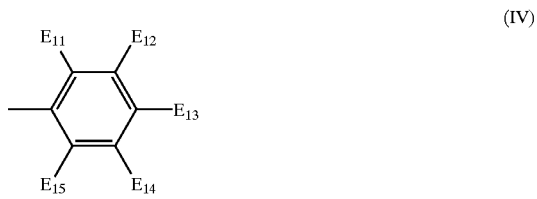

$E_{11}$ to $E_{15}$ are independently hydrogen, F, Cl, Br, nitro, cyano, hydroxyl, carboxyl, alkylthio of 1 to 18 carbon atoms, or alkoxy or 1 to 18 carbon atoms;

when b is 1, E—OH is respectively a carbon-centered radical formed from 2-methyl-2-propanol, 2-propanol, 2,2-dimethyl-1-propanol, 2-methyl-2-butanol, ethanol, 1-propanol, 1-butanol, 1-pentanol, 1-hexanol, 1-nonanol, 1-decanol, 1-dodecanol, 1-octadecanol, 2-butanol, 2-pentanol, 2-ethyl-1-hexanol, cyclohexanol, cyclooctanol, allyl alcohol, phenethyl alcohol or 1-phenyl-1-ethanol;

when b is 2, E—OH is respectively a carbon-centered radical or diradical formed from 1,2-ethanediol, 1,2-propanediol, 1,3-propanediol, 1,2-butanediol, 1,3-butanediol, 1,4-butanediol, 2,2-dimethyl-1,3-propanediol, 1,2-cyclohexanediol, 1,3-cyclohexanediol or 1,4-cyclohexanediol;

when b is 3, E—OH is respectively a carbon-centered radical formed from glycerol, 1,1,1-tris(hydroxymethyl)methane, 2-ethyl-2-hydroxymethyl-1,3-propanediol, 1,2,4-butanetriol or 1,2,6-hexanetriol;

m is 1 to 4;

p is 1 to 4;

$T_1$ is straight or branched chain alkyl of 19 to 80 carbon atoms or a mixture of such alkyl moieties; or $T_1$ is —(R—O)$_n$—R—OG$_5$ where R is ethylene or propylene and n is 4 to 49 so that the total number of carbon atoms in $T_1$ is at least 20;

$G_5$ is hydrogen, straight or branched chain alkyl of 1 to 24 carbon atoms;

X and $X_1$ are independently —O—, or —N—($R_4$)—;

$R_4$ is hydrogen, alkyl of 1 to 18 carbon atoms;

$R_7$ and $R_8$ are independently alkoxy of 1 to 18 carbon atoms, —O—$T_2$, amino substituted by 2-hydroxyethyl, —NH(alkyl) of 1 to 18 carbon atoms, —N(alkyl)$T_2$ with alkyl of 1 to 18 carbon atoms, —X—$T_1$, X—$(CH_2)_m$—CO—$X_1$—$T_1$, or X—$(CH_2)_p$—$X_1$—CO—$T_1$;

$R_9$ is a divalent oxygen atom, or $R_9$ is a divalent nitrogen atom substituted by either hydrogen, alkyl of 1 to 12 carbon atoms or $T_2$

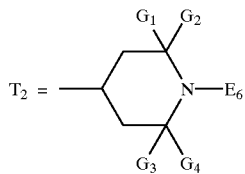

$E_6$ is hydrogen, oxyl, hydroxyl, straight or branched chain alkyl of 1 to 24 carbon atoms, straight or branched chain alkenyl of 3 to 24 carbon atoms, acetyl, —$OE_9$, or, —OE(OH)$_b$;

$R_{10}$ is hydrogen or an alkyl group of 1 to 18 carbon atoms, q is 4 to 8;

y is 1 to 10;

$R_{15}$ is morpholino, piperidino, 1-piperizinyl, alkylamino of 1 to 8 carbon atoms, especially branched alkylamino of 3 to 8 carbon atoms such as tert-octylamino, —X—$T_1$, X—$(CH_2)_m$—CO—$X_1$—$T_1$, or X—$(CH_2)_p$—$X_1$—CO—$T_1$;

$R_{16}$ is hydrogen, acyl of 2 to 4 carbon atoms, carbamoyl substituted by alkyl of 1 to 4 carbon atoms, s-triazinyl substituted once by chlorine and once by $R_{15}$;

$R_{17}$ is amino substituted by alkyl of 1 to 18 carbon atoms or by $T_2$, —N(alkyl)$T_2$ with alkyl of 1 to 8 carbon atoms, —N(alkyl)$_2$ of 2 to 16 carbon atoms, or the group $T_3$

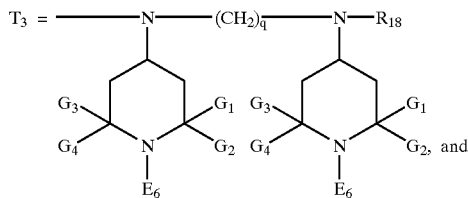

Still other embodiments of formula (1) are

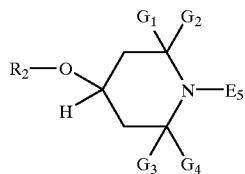

(1)

$G_1$, $G_2$, $G_3$, and $G_4$ are each methyl;

$E_5$ is $OE_9$ or —O—E—(OH)$_b$;

$E_9$ is straight or branched chain alkyl of 1 to 12 carbon atoms, or cycloalkyl of 5 to 10 carbon atoms;

b is 1;

when b is 1, E—OH is respectively a carbon-centered radical formed from 2-methyl-2-propanol;

$R_2$ is —CO—$T_1$;

$T_1$ is straight or branched chain alkyl of 19 to 60 carbon atoms, or a mixture of such alkyl moieties.

Still other embodiments of formula (2) are

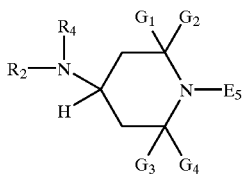

$G_1$, $G_2$, $G_3$, and $G_4$ are each methyl;

$E_5$ is $OE_9$ or —O—E—(OH)$_b$;

$E_9$ is straight or branched chain alkyl of 1 to 12 carbon atoms, or cycloalkyl of 5 to 10 carbon atoms;

b is 1;

when b is 1, E—OH is respectively a carbon-centered radical formed from 2-methyl-2-propanol;

$R_2$ is —CO—$T_1$;

$T_1$ is straight or branched chain alkyl of 19 to 60 carbon atoms, or a mixture of such alkyl moieties; or $R_4$ is hydrogen or methyl.

Still other embodiments of formula (3) are

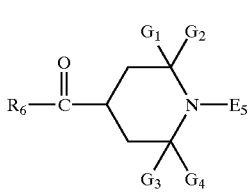

(3)

$G_1$, $G_2$, $G_3$, and $G_4$ are each methyl;

$E_5$ is $OE_9$ or —O—E—(OH)$_b$;

$E_9$ is straight or branched chain alkyl of 1 to 12 carbon atoms, or cycloalkyl of 5 to 10 carbon atoms, b is 1;

when b is 1, E—OH is respectively a carbon-centered radical formed from 2-methyl-2-propanol or 2-propanol;

$T_1$ is straight or branched chain alkyl of 19 to 60 carbon atoms, or a mixture of such alkyl moieties;

X is —O—; and $R_6$ is —X—$T_1$.

Still other embodiments of formula (4) are

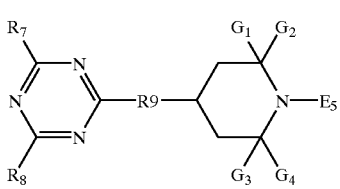

(4)

$G_1$, $G_2$, $G_3$, and $G_4$ are each methyl;

$E_5$ is $OE_9$ or —O—E—(OH)$_b$;

$E_9$ is straight or branched chain alkyl of 1 to 12 carbon atoms, or cycloalkyl of 5 to 10 carbon atoms, b is 1;

when b is 1, E—OH is respectively a carbon-centered radical formed from 2-methyl-2-propanol;

$T_1$ is straight or branched chain alkyl of 19 to 60 carbon atoms, or a mixture of such alkyl moieties; or X and $X_1$ are independently —O—, or —N—($R_4$)—;

$R_4$ is hydrogen or methyl;

$R_7$ and $R_8$ are independently —O—$T_2$, —N(alkyl)$T_2$ with alkyl of 1 to 18 carbon atoms, —X—$T_1$, or X—(CH$_2$)$_p$—$X_1$—CO—$T_1$;

$R_9$ is a divalent oxygen atom, or $R_9$ is a divalent nitrogen atom substituted by either hydrogen, alkyl of 1 to 12 carbon atoms or $T_2$

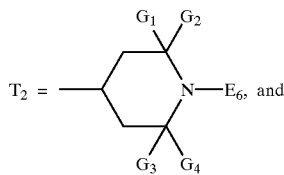

$E_6$ is hydrogen, hydroxyl, straight or branched chain alkyl of 1 to 12 carbon atoms, acetyl, —OE$_9$, or —OE(OH)$_b$.

In another embodiment of the instant invention, the long chain hindered amine compound is (a) 2,4-bis[N-n-butyl—N—(1-cyclohexyloxy-2,2,6,6-tetramethylpiperidin-4-yl)amino]-6-[2-(C$_{20}$–C$_{40}$alkanoyloxy)ethyl]amino-s-triazine;

(b) 1-cyclohexyloxy-2,2,6,6-tetramethyl-4-C$_{20}$–C$_{40}$alkanoyloxypiperidine;

(c) 4-C$_{40}$–C$_{60}$oalkanoyloxy-2,2,6,6-tetramethyl-1-methoxypiperidine;

(d) 4-C$_{20}$–C$_{40}$alkanoyloxy-2,2,6,6-tetramethyl-1-octyloxypiperidine;

(e) 4-C$_{20}$–C$_{40}$alkanoyloxy-2,2,6,6-tetramethyl-1-(2-methyl-2-hydroxypropyloxy)piperidine;

(f) 4-C$_{40}$–C$_{60}$alkanoyloxy-2,2,6,6-tetramethyl-1-(2-methyl-2-hydroxypropyloxy)piperidine;

(g) 4-(N-methyl—N—C$_{20}$–C$_{40}$alkanoyl)amino-2,2,6,6-tetramethyl-1-methoxypiperidine;

(h) 4-(N-methyl—N—C$_{20}$–C$_{40}$oalkanoyl)amino-2,2,6,6-tetramethyl-1-(2-methyl-2-hydroxy-propyloxy)piperidine;

(i) C$_{20}$–C$_{40}$alkyl 1-methoxy-2,2,6,6-tetramethylpiperidin-4-ylcarboxylate;

(j) C$_{40}$–C$_{60}$alkyl 1-cyclohexyloxy-2,2,6,6-tetramethylpiperidin-4-ylcarboxylate;

(k) C$_{20}$–C$_{40}$alkyl 1-(2-methyl-2-hydroxypropyloxy)-2,2,6,6-tetramethylpiperidin-4-yl-carboxylate;

(l) 2,4-bis[N-n-butyl—N—(1-methoxy-2,2,6,6-tetramethylpiperidin-4-yl)amino]-6-[2-(C$_{20}$–C$_{40}$alkanoyloxy)ethyl]amino-s-triazine;

(m) 2,4-bis(1-octyloxy-2,2,6,6-tetramethylpiperidin-4-yloxy)-6-(C$_{20}$–C$_{40}$alkyloxy)-s-triazine;

(o) 2,4-bis{N-n-butyl—N—[1-(2-methyl-2-hydroxypropyloxy)-2,2,6,6-tetramethylpiperidin-4-yl]amino}-6-[2-(C$_{20}$–C$_{40}$alkanoyloxy)ethyl]amino-s-triazine; or (p) 2,4-bis[1-(2-methyl-2-hydroxypropyloxy)-2,2,6,6-tetramethylpiperidin-4-yloxy)-6-(C$_{40}$–C$_{60}$alkyloxy)-s-triazine.

In still another embodiment of the instant invention, the long chain hindered amine compound is (a) 2,4-bis[N-n-butyl—N—(1-cyclohexyloxy-2,2,6,6-tetramethylpiperidin-4-yl)amino]-6-[2-(C$_{20}$–C$_{40}$alkanoyloxy)ethyl]amino-s-triazine; or (b) 1-cyclohexyloxy-2,2,6,6-tetramethyl-4-C$_{20}$–C$_{40}$alkanoyloxypiperidine.

The instant invention pertains to a composition which comprises (a) candle wax which is white and unscented; white and scented; dyed and unscented; dyed and scented; dipped and unscented; or dipped and scented, and (b) an effective stabilizing amount of a combination of
(i) a long chain hindered amine piperidine compound of formula 1, 2, 3, 4, 5 or 6 as described above;
(ii) a UV absorber or an antioxidant, or a UV absorber and an antioxidant wherein the ratio by weight of (i) to (ii) is from 10:1 to 1:10.

It should be noted that, although the long chain hindered amines described in detail in this application are those derived from 2,2,6,6-tetraalkylpiperidine moieties, other types of hindered amines such as those containing morpholinones, piperazinones, piperazindiones, oxazolidines, imidazolines and the like could also be modified to attached long chain alkyl moieties which would make them particularly suitable for the stabilization of thermoplastic resins such as polyolefins or polyesters and the stabilization of candle wax.

In another embodiment of the invention, the ratio by weight of (i) to (ii) is from 4:1 to 1:4.

Another embodiment of the invention is where the ratio by weight of (i) to (ii) is from 2:1 to 1:2.

In still another embodiment of the invention, the effective amount of the UV absorber plus the long chain hindered amine compound in the candle wax is 0.01 to 10% by weight based on the wax.

Another embodiment of the invention is where the effective amount of the UV absorber plus long chain hindered amine compound in the candle wax is 0.1 to 2% by weight based on the wax.

Another embodiment of the invention is where the effective amount of the UV absorber plus long chain hindered amine compound in the candle wax is 0.1 to 0.5% by weight based on the wax.

The UV absorber of component (ii) is a benzotriazole, a benzophenone, an α-cyanoacrylate, an oxanilide, an s-triazine, a cinnamate, a malonate, a benzoate or a salicylate, or a mixture thereof.

In another embodiment of the invention, the UV absorber is a benzotriazole, a benzophenone or an s-triazine.

Examples of the UV absorbers useful in the instant invention are (a) 4-octyloxy-2-hydroxybenzophenone;

(b) 4-methoxy-2-hydroxybenzophenone;

(c) 2-(2-hydroxy-5-methylphenyl)-2H-benzotriazole;

(d) 2-(2-hydroxy-5-tert-octylphenyl-2H-benzotriazole;

(e) 2-(2-hydroxy-3,5-di-tert-amylphenyl)-2H-benzotriazole;

(f) octyl 3-(benzotriazol-2-yl)-5-tert-butyl-4-hydroxyhydrocinnamate;

(g) 2-(2-hydroxy-3,5-di-tert-butylphenyl)-2H-benzotriazole;

(h) 2-(2-hydroxy-5-tert-butylphenyl)-2H-benzotriazole;

(i) 5-chloro-2-(2-hydroxy-3,5-di-tert-butylphenyl)-2H-benzotriazole;

(j) 5-chloro-2-(2-hydroxy-3-tert-butyl-5-methylphenyl)-2H-benzotriazole;

(k) 2-(2-hydroxy-3-sec-butyl-5-tert-butylphenyl)-2H-benzotriazole;

(l) 2-(2-hydroxy-4-octyloxyphenyl)-2H-benzotriazole;

(m) 2-(2-hydroxy-3-dodecyl-5-methylphenyl)-2H-benzotriazole;
(n) 2-[2-hydroxy-3,5-di(α,α-dimethylbenzyl)phenyl]-2H-benzotriazole;
(o) 2-[2-hydroxy-3-(α,α-dimethylbenzyl)-5-tert-octylphenyl]-2H-benzotriazole;
(p) 2-{2-hydroxy-3-tert-butyl-5-[2-(omega-hydroxy-octa(ethyleneoxy)carbonyl)ethyl]-phenyl}-2H-benzotriazole;
(q) 2-{2-hydroxy-3-tert-butyl-5-[2-(octyloxy)carbonyl)ethyl]phenyl}-2H- benzotriazole.
(r) 2-ethylhexyl p-methoxycinnamate;
(s) 4-methoxy-2,2'-dihydroxybenzophenone;
(t) 4,4'dimethoxy-2,2'-dihydroxybenzophenone;
(u) 2,4-bis(2,4-dimethylphenyl)-6-(2-hydroxy-4-octyloxyphenyl)-s-triazine;
(v) 2,4-diphenyl-6-(2-hydroxy-4-hexyloxyphenyl)-s-triazine;
(w) 2,4-bis(2,4-dimethylphenyl)-6-[2-hydroxy-4-(3-do-/tri-decyloxy-2-hydroxypropoxy)-phenyl]-s-triazine;
(x) 2,4-bis(2,4-dimethylphenyl)-6-[2-hydroxy-4-(3-do-/tri-decyloxy-2-hydroxypropoxy)-5-α-cumylphenyl]-s-triazine;
(y) reaction product of 2,4,6-tris(2,4-dihydroxyphenyl)-s-triazine with octyl α-haloacetate; or
(z) the mixture of 3,3;3,5;5,5-methylene-bis[2,4-bis(2,4-dimethylphenyl)]-6-[2-hydroxy-4-(3-butyloxy-2-hydroxypropoxyphenyl)]-s-triazine.

Still other examples of UV absorbers useful in the instant invention are
(a) 4-octyloxy-2-hydroxybenzophenone;
(b) 4-methoxy-2-hydroxybenzophenone;
(d) 2-(2-hydroxy-5-tert-octylphenyl-2H-benzotriazole;
(o) 2-[2-hydroxy-3-(α,α-dimethylbenzyl)-5-tert-octylphenyl]-2H-benzotriazole;
(p) 2-{2-hydroxy-3-tert-butyl-5-[2-(omega-hydroxy-octa(ethyleneoxy)carbonyl)ethyl]-phenyl}-2H-benzotriazole;
(q) 2-{2-hydroxy-3-tert-butyl-5-[2-(octyloxy)carbonyl)ethyl]phenyl}-2H-benzotriazole;
(y) reaction product of 2,4,6-tris(2,4-dihydroxyphenyl)-s-triazine with octyl a-haloacetate; or
(z) the mixture of 3,3;3,5;5,5-methylene-bis[2,4-bis(2,4-dimethylphenyl)]-6-[2-hydroxy-4-(3-butyloxy-2-hydroxypropoxyphenyl)]-s-triazine.

Another embodiment of the instant invention involves a composition wherein the antioxidant is a phenolic antioxidant, phosphite, nitrone, amine oxide or hydroxylamine, or mixture thereof.

Examples of the above-embodiment are wherein the effective amount of UV absorber in combination with the long chain hindered amine compound and an antioxidant is 0.01 to 10% by weight based on the wax.

Another embodiment is where the effective amount of UV absorber in combination with the long chain hindered amine compound and an antioxidant is 0.1 to 2% by weight based on the wax.

Still another embodiment is where the effective amount of UV absorber in combination with the long chain hindered amine compound and an antioxidant is 0.1 to 0.5% by weight based on the wax.

Examples of the antioxidants useful in this invention are
n-octadecyl 3,5-di-tert-butyl-4-hydroxyhydrocinnamate,
neopentanetetrayl tetrakis(3,5-di-tert-butyl-4-hydroxyhydrocinnammate),
di-n-octadecyl 3,5-di-tert-butyl-4-hydroxybenzylphosphonate,
1,3,5-tris(3,5-di-tert-butyl-4-hydroxybenzyl) isocyanurate,
thiodiethylene bis(3,5-di-tert-butyl-4-hydroxyhydrocinnamate),
1,3,5-trimethyl-2,4,6-tris(3,5-di-tert-butyl-4-hydroxybenzyl)benzene,
3,6-dioxaoctamethylene bis(3-methyl-5-tert-butyl-4-hydroxyhydrocinnamate),
2,6-di-tert-butyl-p-cresol,
2,2'-ethylidene-bis(4,6-di-tert-butylphenol),
1,3,5-tris(2,6-dimethyl-4-tert-butyl-3-hydroxybenzyl) isocyanurate,
1,1,3,-tris(2-methyl-4-hydroxy-5-tert-butylphenyl) butane,
1,3,5-tris[2-(3,5-di-tert-butyl-4-hydroxyhydrocinnamoyloxy)ethyl] isocyanurate,
3,5-di-(3,5-di-tert-butyl-4-hydroxybenzyl)mesitol,
hexamethylene bis(3,5-di-tert-butyl-4-hydroxyhydrocinnamate),
1-(3,5-di-tert-butyl-4-hydroxyanilino)-3,5-di(octylthio)-s-triazine,
N,N'-hexamethylene-bis(3,5-di-tert-butyl-4-hydroxyhydrocinnamamide),
calcium bis(ethyl 3,5-di-tert-butyl-4-hydroxybenzylphosphonate),
ethylene bis[3,3-di(3-tert-butyl-4-hydroxyphenyl) butyrate],
octyl 3,5-di-tert-butyl-4-hydroxybenzylmercaptoacetate,
bis(3,5-di-tert-butyl-4-hydroxyhydrocinnamoyl) hydrazide,
N,N-di-($C_{12}$–$C_{24}$alkyl)—N—methyl-amine oxide, or
N,N-dialkylhydroxylamine prepared from di(hydrogenated tallow)amine by direct oxidation.

Still other embodiments of antioxidants useful in the instant invention are
neopentanetetrayl tetrakis(3,5-di-tert-butyl-4-hydroxyhydrocinnamate),
n-octadecyl 3,5-di-tert-butyl-4-hydroxyhydrocinnamate,
1,3,5-trimethyl-2,4,6-tris(3,5-di-tert-butyl-4-hydroxybenzyl)benzene,
1,3,5-tris(3,5-di-tert-butyl-4-hydroxybenzyl) isocyanurate,
2,6-di-tert-butyl-p-cresol, or
2,2'-ethylidene-bis(4,6-di-tert-butylphenol).

The instant invention pertains to a composition which comprises
(a) a thermoplastic resin, and
(b) an effective stabilizing amount of a combination of a long chain hindered amine piperidine compound of formula 1, 2, 3, 4, 5 or 6 as described above.

Preferably, the organic material is a natural, semi-synthetic or synthetic polymer, especially a thermoplastic polymer.

Most preferably, the polymer is a polyolefin or polycarbonate, especially polyethylene or polypropylene; most especially polypropylene.

In another preferred embodiment of the instant invention, the organic material is a resin selected from the group consisting of a thermoset acrylic melamine resin, an acrylic urethane resin, an epoxy carboxy resin, a silane modified acrylic melamine, an acrylic resin with carbamate pendant groups crosslinked with melamine or an acrylic polyol resin crosslinked with melamine containing carbamate groups.

Most preferably, the resin is a thermoset acrylic melamine resin or an acrylic urethane resin.

In yet another preferred embodiment of the instant invention, the organic material is a recording material.

The recording materials according to the invention are suitable for pressure-sensitive copying systems, photocopying systems using microcapsules, heat-sensitive copying systems, photographic materials and ink jet printing.

The recording materials according to the invention are distinguished by an unexpected improvement in quality, especially with regard to the fastness to light.

The recording materials according to the invention have the construction known for the particular use. They consist of a customary carrier, for example, paper or plastic film, which has been coated with one or more layers. Depending on the type of material, these layers contain the appropriate necessary components, in the case of photographic materials, for example, silver halide emulsions, dye couplers, dyes and the like. Material particularly suitable for ink jet printing has a layer particularly absorptive for ink on a customary carrier. Uncoated paper can also be employed for ink jet printing. In this case the paper acts at the same time as the carrier material and as the ink-absorbent layer. Suitable material for ink jet printing is, for example, described in U.S. Pat. No. 5,073,448 which is incorporated herein by reference.

The recording material can also be transparent as, for example, in the case of projection films.

The compounds of formula 1,2,3,4,5 or 6 can be incorporated into the carder material as early as the production of the latter, in the production of paper, for example, being added to the paper pulp. A second method of application is to spray the carder material with an aqueous solution of compounds of formula 1,2,3,4,5 or 6 or to add the compounds to the coating composition.

Coating compositions intended for transparent recording materials suitable for projection cannot contain any particles which scatter light, such as pigments and fillers.

The dye-binding coating composition can contain a number of other additives, for example, antioxidants, light stabilizers (including also UV absorbers which do not fall under the scope of the UV absorbers of this invention), viscosity improvers, fluorescent brighteners, biocides and/or antistatic agents.

The coating composition is usually prepared as follows: the water-soluble components, for example, the binder, are dissolved in water and stirred together; the solid components, for example, fillers and other additives already described, are dispersed in this aqueous medium; and disperison is advantageously carried out by means of devices, for example, ultrasonic systems, turbine stirrers, homogenizers, colloid mills, bead mills, sand mills, highspeed stirrers and the like. The compounds of formula 1,2,3,4,5 or 6 can be easily incorporated into the coating composition.

The recording material according to this invention preferably contains 1 to 5000 mg/m$^2$, in particular 50–1200 mg/m$^2$, of a compound of formula 1,2,3,4,5 or 6.

As already mentioned, the recording materials according to the invention embrace a wide field. The compounds of formula 1,2,3,4,5 or 6 can, for example, be employed in pressure-sensitive copying systems. They can be introduced either into the paper in order to protect the microencapsulated dye precursors there from light, or into the binder of the developer layer in order to protect the dyes formed there.

Photocopying systems using light-sensitive microcapsules which are developed by means of pressure are described in U.S. Pat. Nos. 4,416,966; 4,483,912; 4,352,200; 4,535,050; 4,535,463; 4,551,407; 4,562,137 and 4,608,330; and also in EP-A 139,479; EP-A 162,664; EP-A 164,931; EP-A 237,024; EP-A 237,025 and EP-A 260,129. In all these systems, the compounds can be put into the dye-receiving layer. The compounds can, however, also be put into the donor layer in order to protect the color formers from light.

Photographic materials which can be stabilized are photographic dyes and layers containing such dyes or precursors thereof, for example, photographic paper and films. Suitable materials are, for example, described in U.S. Pat. No. 5,364,749 which is incorporated herein by reference. In color photographic materials, couplers and dyes are also protected against photochemical decomposition.

The instant compounds can be used for all types of color photographic materials. For example, they can be employed for color paper, color reversal paper, direct-positive color material, color negative film, color positive film, color reversal film and the like. They are preferably used inter alia for photographic color material which contains a reversal substrate or form positives.

Color-photographic recording materials usually contain, on a support, a blue-sensitive and/or a green-sensitive and/or a red-sensitive silver halide emulsion layer and, if desired, a protection layer, with the instant compounds being, preferably, either in the green-sensitive or the red-sensitive layer or in a layer between the green-sensitive and the red-sensitive layer or in a layer on top of the silver halide emulsion layers.

The compounds of formula 1,2,3,4,5 or 6 can also be employed in recording materials based on the principles of photopolymerization, photoplasticization or the rupture of microcapsules, or in cases where heat-sensitive and light-sensitive diazonium salts, leuko dyes having an oxidizing agent or dye lactones having Lewis acids are used.

Furthermore, the instant compounds can be employed in recording materials for dye diffusion transfer printing, thermal wax transfer printing and non-matrix printing and for use with electrostatic, electrographic, electrophoretic, magnetographic and laser-electrophotographic printers and penplotters. Of the above, recording materials for dye diffusion transfer printing are preferred, for example, as described in EP-A 507,734.

The instant compounds can also be employed in inks, preferably for ink jet printing, for example, as described in U.S. Pat. No. 5,098,477 which is incorporated herein by reference.

The compounds of this invention exhibit superior hydrolytic stability, handling and storage stability as well as good resistance to extractability when present in a stabilized composition.

The methodology to make the instant compounds is described in the prior art. The intermediates needed to make the instant compounds are largely items of commerce.

In general polymers which can be stabilized include
1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:
 a) radical polymerisation (normally under high pressure and at elevated temperature).
 b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisabon or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/iso-butylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid co-polymers (EM), LLDPE/EVA, LLDPE/EM and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/-acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/ styrene.

7. Graft copolymers of styrene or a-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrile/vinyl halide copolymers or acrylonitrile/ alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand and phenols, ureas and melamines on the other hand, such as phenol/formaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, polyisocyanates or epoxy resins.
26. Crosslinked epoxy resins derived from polyepoxides, for example from bisglycidyl ethers or from cycloaliphatic diepoxides.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/-EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.
31. Polysiloxanes such as the soft, hydrophilic polysiloxanes described, for example, in U.S. Pat. No. 4,259,467; and the hard polyorganosiloxanes described, for example, in U.S. Pat. No. 4,355,147.
32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
33. Radiation curable compositions containing ethylenically unsaturated monomers or oligomers and a polyunsaturated aliphatic oligomer.
34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
    1.1. Alkylated monophenols, for example,
        2,6-di-tert-butyl-4-methylphenol
        2-tert-butyl-4,6-dimethylphenol
        2,6-di-tert-butyl-4-ethylphenol
        2,6-di-tert-butyl-4-n-butylphenol
        2,6-di-tert-butyl-4-i-butylphenol
        2,6-di-cyclopentyl-4-methylphenol
        2-($\alpha$-methylcyclohexyl)-4,6-dimethylphenol
        2,6-di-octadecyl-4-methylphenol
        2,4,6-tri-cyclohexylphenol
        2,6-di-tert-butyl-4-methoxymethylphenol
    1.2. Alkylated hydroquinones, for example,
        2,6-di-tert-butyl-4-methoxyphenol
        2,5-di-tert-butyl-hydroquinone
        2,5di-tert-amyl-hydroquinone
        2,6-diphenyl-4-octadecyloxyphenol
    1.3. Hydroxylated thiodiphenyl ethers, for example,
        2,2'-thio-bis-(6-tert-butyl-4-methylphenol)
        2,2'-thio-bis-(4-octylphenol)
        4,4'-thio-bis-(6-tert-butyl-3-methylphenol)

4,4'-thio-bis-(6-tert-butyl-2-methylphenol)

1.4. Alkylidene-bisphenols, for example, 2,2'-methylene-bis-(6-tert-butyl-4-methylphenol)

2,2'-methylene-bis-(6-tert-butyl-4-ethylphenol)

2,2'-methylene-bis-[4-methyl-6-(α-methylcyclohexyl)-phenol]

2,2'-methylene-bis-(4-methyl-6-cyclohexylphenol)

2,2'-methylene-bis-(6-nonyl-4-methylphenol)

2,2'-methylene-bis-[6-(α-methylbenzyl)-4-nonylphenol]

2,2'-methylene-bis-[6-(α,α-dimethylbenzyl)-4-nonylphenol]

2,2'-methylene-bis-(4,6-di-tert-butylphenol)

2,2'-ethylidene-bis-(4,6-di-tert-butylphenol)

2,2'-ethylidene-bis-(6-tert-butyl-4-isobutylphenol)

4,4'-methylene-bis-(2,6-di-tert-butylphenol)

4,4'-methylene-bis-(6-tert-butyl-2-methylphenol)

1,1-bis-(5-tert-butyl-4-hydroxy-2-methylphenyl)-butane 2,6-di-(3-tert-butyl-5-methyl-2-hydroxybenzyl)-4-methylphenol 1,1,3-tris-(5-tert-butyl-4-hydroxy-2-methylphenyl)-butane 1,1-bis-(5-tert-butyl-4-hydroxy-2-methylphenyl)-3-n-dodecylmercaptobutane ethyleneglycol bis-[3,3-bis-(3'-tert-butyl-4'-hydroxyphenyl)-butyrate]

di-(3-tert-butyl-4-hydroxy-5-methylphenyl)-dicyclopentadiene di-[2-(3'-tert-butyl-2'-hydroxy-5'-methyl-benzyl)-6-tert-butyl-4-methylphenyl] terephthalate.

1.5. Benzyl compounds, for example, 1,3,5-tri-(3,5-di-tert-butyl-4-hydroxybenzyl)-2,4,6-trimethylbenzene di-(3,5-di-tert-butyl-4-hydroxybenzyl) sulfide 3,5-di-tert-butyl-4-hydroxybenzyl-mercapto-acetic acid isooctyl ester bis-(4-tert-butyl-3-hydroxy-2,6-dimethylbenzyl)dithiol terephthalate 1,3,5-tris-(3,5-di-tert-butyl-4-hydroxybenzyl) isocyanurate 1,3,5-tris-(4-tert-butyl-3-hydroxy-2,6-dimethylbenzyl) isocyanurate 3,5-di-tert-butyl-4-hydroxybenzyl-phosphoric acid dioctadecyl ester 3,5-di-tert-butyl-4-hydroxybenzyl-phosphoric acid monoethyl ester, calcium-salt 1.6. Acylaminophenols, for example, 4-hydroxy-lauric acid anilide 4-hydroxy-stearic acid anilide 2,4-bis-octylmercapto-6-(3,5-tert-butyl-4-hydroxyanilino)-s-triazine octyl—N—(3,5-di-tert-butyl-4-hydroxyphenyl)-carbamate 1.7. Esters of β-(3.5-di-tert-butyl-4-hydroxyphenyl)-propionic acid with monohydric or polyhydric alcohols, for example,

| methanol | diethylene glycol |
|---|---|
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.8. Esters of β-(5-tert-butyl-4-hydroxy-3-methylphenyl)-propionic acid with monohydric or polyhydric alcohols, for example,

| methanol | diethylene glycol |
|---|---|
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.9. Amides of β-(3.5-di-tert-butyl-4-hydroxyphenyl)-propionic acid for example, N,N'-di-(3,5-di-tert-butyl-4-hydroxyphenylpropionyl)-hexamethylenediamine N,N'-di-(3,5-di-tert-butyl-4-hydroxyphenylpropionyl)-trimethylenediamine N,N'-di-(3,5-di-tert-butyl-4-hydroxyphenylpropionyl)-hydrazine 1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl )-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, a-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetra-methylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1' (1,2-ethanediyl)-bis-(3,3,5,5-tetramethylpiperazinone), bis (1-octyloxy-2,2,6,6-tetramethylpiperidin-4-yl) sebacate.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy—as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxy-ethoxy)phenyl]-6-(4-chlorophenyl)-s-triazine; 2,4-bis[2-hydroxy-4-(2-hydroxy-4-(2-hydroxy-ethoxy)phenyl]-6-(2,4-dimethylphenyl)-s-triazine; 2,4-bis[2-hydroxy-4-( 2-hydroxyethoxy)phenyl]-6-(4-bromophenyl)-s-triazine; 2,4-bis[2-hydroxy-4-(2-acetoxyethoxy)phenyl]-6-(4-chloropheny)-s-triazine, 2,4-bis(2,4-dihydroxyphenyl)-6-(2, 4-dimethylphenyl)-s-triazine.

3. Metal deactivators, for example, N,N'-diphenyloxalic acid diamide, N-salicylal-N'-salicyloyl-hydrazine, N,N'-bis-salicyloylhydrazine, N,N'bis-(3,5-di-tert-butyl-4-hydroxyphenylpropionyl)-hydrazine, 3-salicyloylamino-1, 2,4-triazole, bis-benzylidene-oxalic acid dihydrazide.

4. Phosphites and phosphonites, for example, triphenyl phosphite, diphenylalkyl phosphites, phenyidialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecyl-pentaerythritol diphosphite, di-(2,4,6-tri-tert-butylphenyl)-pentaerythritol diphosphite, di-(2,4-di-tert-butyl-6-methylphenyl)-pentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl—N—octadecylhydroxyl-amine, N-heptadecyl—N—octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylinitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

13. Benzofuranones and indolinones, for example those disclosed in U.S. Pat. No. 4,325,863, U.S. Pat. No. 4,338, 244 or U.S. Pat. No. 5,175,312, or 3-[4-(2-acetoxyethoxy) phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl) benzofuran-2-one], 5,7-di-tert-butyl-3-(4-ethoxyphenyl) benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofu ran-2-one.

The co-stabilizers, with the exception of the benzofuranones listed under 13, are added for example in concentrations of 0.01 to 10%, relative to the total weight of the material to be stabilized.

Further preferred compositions comprise, in addition to components (a) and (b) further additives, in particular phenolic antioxidants, light stabilizers or processing stabilizers.

Particularly preferred additives are phenolic antioxidants (item 1 of the list), sterically hindered amines (item 2.6 of the list), phosphites and phosphonites (item 4 of the list) and peroxide-destroying compounds (item 5.) of the list.

Additional additives (stabilizers) which are also particularly preferred are benzofuran-2-ones, such as described, for example, in U.S. Pat. No. 4,325,863, U.S. Pat. No. 4,338, 244 or U.S. Pat. No. 5,175,312.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3, 5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)

benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris-[2-(3,5-di-tert-butyl-4-hydroxyhydrocinnamoyloxy)ethyl]isocyanur ate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-eth yl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dio ne, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.1 1.2]heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N",N"'4etrakis[(4,6-bis(butyl-1,2,2,6,6-pentamethylpiperidin-4-yl)-amino-s-triazin-2-y 1]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5-undecane) diethyl] 1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]undecane)diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-yln-dodecylsuccinimide, 1-acetyl3-dodecyl-7,7,9,9-tetramethyl-1,3,8-triazaspiro[4.5]decane-2,4-dione, di-(1-octyloxy-2,2,6,6-tetramethylpiperidin-4-yl)sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethyl-piperidin-4-yl) imino], and 2,4,6-tris[N-(1-cyclohexyloxy-2,2,6,6-tetramethylpiperidin-4-yl)-n-butylamino]-s-triazine, bis[1-(2-hydroxy-2-methylpropoxy)-2,2,6,6-tetramethylpiperidin-4-yl)]sebacate; a mixture of bis[1-(2-hydroxy-2-methylpropoxy)-2,2,6,6-tetramethylpiperidin-4-yl]glutarate and bis[1-(2-hydroxy-2-methylpropoxy)-2,2,6,6-tetramethylpiperidin-4-yl] adipate; 1-(2-hydroxy-2-methylpropoxy)-4-octadecanoyloxy-2,2,6,6-tetramethylpiperidine; bis[1-(2-hydroxy-2-methylpropoxy)-2,2,6,6-tetramethylpiperidin-4-yl] adipate; bis[1-(2-hydroxy-2-methyl-propoxy)-2,2,6,6-tetramethylpiperidin-4-yl] glutarate; bis[1-(2-hydroxy-2-methylpropoxy)- 2,2,6,6-tetramethylpiperidin-4-yl] succinate; a mixture of bis[1-(2-hydroxy-2-methylpropoxy)-2,2,6,6-tetramethylpiperidin-4-yl] glutarate and bis[1-(2-hydroxy-2-methylpropoxy)-2,2,6,6-tetramethyl-piperidin-4-yl] succinate; 1-(4-octadecanoyloxy-2,2,6,6-tetramethylpiperidin-1-yloxy)-2-octa-decanoyloxy-2-methylpropane; 1-(2-hydroxy-2-methylpropoxy)-4-[9-(methoxy-carbonyl)-nonanoyloxy]-2,2,6,6-tetramethylpiperidine; 1-(2-hydroxy-2-methylpropoxy)-4-[5-(methoxy-carbonyl)pentanoyloxy]-2,2,6,6-tetramethylpiperidine; 1-(2-hydroxy-2-methylpropoxy)-4-[3-(methoxy-carbonyl)propionyloxy]-2,2,6,6-tetramethylpiperidine; 1-(2-hydroxy-2-methylpropoxy)-4-[4-(methoxy-carbonyl)butyryloxy]-2,2,6,6-tetramethylpiperidine; condensation product of 4-hydroxy-1-(2-hydroxy-2-methylpropoxy)-2,2,6,6-tetramethylpiperidine with hexamethylene diisocyanate and terminated with methoxy; condensation product of 4-hydroxy-1-(2-hydroxy-ethoxy)-2,2,6,6-tetramethylpiperidine with hexamethylene diisocyanate and terminated with methoxy; condensation product of 4-hydroxy-1-(2-hydroxy-1-phenethoxy)-2,2,6,6-tetramethyl-piperidine with hexamethylene diisocyanate and terminated with methoxy; 1-(2-hydroxy-2-methylpropoxy)-4-hexadecanoyloxy-2,2,6,6-tetramethylpiperidine; or 1-(2-hydroxy-2-methylpropoxy-4-hydroxy-2,2,6,6-tetramethylpiperidine.

A most preferred hindered amine compound is bis(2,2,6,6-tetramethylpiperidin-4-yl)sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N",N"'-tetrakis[(4,6-bis(butyl-(1,2,2,6,6-pentamethylpiperidin-4-yl)amino)- s-triazine-2-yl]-1,10-diamino-4,7-diazadecane. di-(1-octyloxy-2,2,6,6-tetramethyl-piperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], or 2,4,6-tris[N-(1-cyclohexyloxy-2,2,6,6-tetramethyl-piperidin-4-yl)-n-butylamino]-s-triazine, bis[1-(2-hydroxy-2-methylpropoxy)-2,2,6,6-tetramethyl-piperidin-4-yl)] sebacate; a mixture of bis[1-(2-hydroxy-2-methylpropoxy)-2,2,6,6-tetramethyl-piperidin-4-yl] glutarate and bis[1-(2-hydroxy-2-methylpropoxy)-2,2,6,6-tetramethylpiperidin-4- yladipate; 1-(2-hydroxy-2-methylpropoxy)-4-octadecanoyloxy-2,2,6,6-tetramethylpiperidine; bis[1-(2-hydroxy-2-methylpropoxy)-2,2,6,6-tetramethylpiperidin-4-yl] adipate; bis[1-(2-hydroxy-2-methylpropoxy)-2,2,6,6-tetramethylpiperidin-4-yl] glutarate; bis[1-(2-hydroxy-2-methylpropoxy)-2,2,6,6-tetramethylpiperidin-4-yl] succinate; a mixture of bis[1-(2-hydroxy-2-methylpropoxy)-2,2,6,6-tetramethylpiperidin-4-yl] glutarate and bis[1-(2-hydroxy-2-methylpropoxy)-2,2,6,6-tetramethylpiperidin-4-yl] succinate; 1-(4-octadecanoyloxy-2,2,6,6-tetramethylpiperidin-1-yloxy)-2-octadecanoyloxy-2-methylpropane; 1-(2-hydroxy-2-methylpropoxy)-4-[9-(methoxy-carbonyl)-nonanoyloxy]-2,2,6,6-tetramethylpiperidine; 1-(2-hydroxy-2-methylpropoxy)-4-[5-(methoxy-carbonyl)pentanoyloxy]-2,2,6,6-tetramethylpiperidine;1-(2-hydroxy-2-methylpropoxy)-4-[3-(methoxy-carbonyl)propionyloxy]-2,2,6,6-tetramethylpiperidine; 1-(2-hydroxy-2-methylpropoxy)-4-[4-(methoxy-carbonyl)butyryloxy]-2,2,6,6-tetramethylpiperidine; condensation product of 4-hydroxy-1-(2-hydroxy-2-methylpropoxy)-2,2,6,6-tetramethylpiperidine with hexamethylene diisocyanate and terminated with methoxy; condensation product of 4-hydroxy-1-(2-hydroxyethoxy)-2,2,6,6-tetramethylpiperidine with hexamethylene diisocyanate and terminated with methoxy; condensation product of 4-hydroxy-1-(2-hydroxy-1-phenethoxy)-2,2,6,6-tetramethyl-piperidine with hexamethylene diisocyanate and terminated with methoxy; 1-(2-hydroxy-2-methylpropoxy)-4-hexadecanoyloxy-2,2,6,6-tetramethylpiperidine; or 1-(2-hydroxy-2-methylpropoxy)-4-hydroxy-2,2,6,6-tetramethylpiperidine.

The instant composition can additionally contain a UV absorber selected from the group consisting of the s-triazines, the oxanilides, the hydroxybenzophenones, benzoates and the α-cyanoacrylates.

Particularly, the instant composition may additionally contain an effective stabilizing amount of at least one other 2-hydroxyphenyl-2H-benzotriazole; another tris-aryl-s-triazine; or hindered amine or mixtures thereof.

Preferably, the 2-hydroxyphenyl-2H-benzotriazole is selected from the group consisting of 2-(2-hydroxy-3,5-di-tert-amylphenyl)-2H-benzotriazole;
2-[2-hydroxy-3,5-di(α,α-dimethylbenzyl)phenyl]-2H-benzotriazole;
2-[2-hydroxy-3-(α,α-dimethylbenzyl)-5-octylphenyl]-2H-benzotriazole;
2-{(2-hydroxy-3-tert-butyl-5-[2-(omega-hydroxy-octa(ethyleneoxy)carbonyl)ethyl]phenyl}-2H-benzotriazole; and
2-{2-hydroxy-3-tert-butyl-5-[2-(octyloxy)carbonyl)ethyl]phenyl}-2H-benzotriazole.

Preferably, the other tris-aryl-s-triazine is selected from the group consisting of 2,4-bis(2,4-dimethylphenyl)-6-(2-hydroxy-4-octyloxyphenyl)-s-triazine;
2,4-diphenyl-6-(2-hydroxy-4-hexyloxyphenyl)-s-triazine; 2,4-bis(2,4-dimethylphenyl)-6-[2-hydroxy-4-(3-do-/tri-decyloxy-2-hydroxypropoxy)phenyl]-s-triazine; and
2-(2-hydroxyethylamino)-4,6-bis[N-butyl—N—(1-cyclohexybxy-2,2,6,6-tetramethylpiperidin-4-yl)amino]-s-triazine.

The alkyd resin lacquers which can be stabilized against the action of light and moisture in accordance with the instant invention are the conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99–123). Other crosslinking agents include glycouril resins, blocked isocyanates or epoxy resins.

The lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the crosslinking agent for various acrylic or polyester resin systems that have been modified by the presence of reactive groups on the backbone structure.

When used in two-coat finishes, the compounds of the instant invention can be incorporated in the clear coat or both in the clear coat and in the pigmented base coat.

When water-soluble, water miscible or water dispersible coating are desired ammonium salts of acid groups present in the resin are formed. Powder coating composition can be prepared by reacting glycidyl methacrylate with selected alcohol components.

The instant invention also pertains to a photographic material stabilized against degradation induced by light which comprises (a) a photographic material, and
(b) an effective stabilizing amount of a compound of formula 1,2,3,4,5 or 6 as defined above.

The instant invention additionally pertains to a composition stabilized against degradation induced by heat, oxygen or light which comprises (a) a thermoset composition, and
(b) an effective stabilizing amount of a compound of formula 1,2,3,4,5 or 6 as defined above.

The thermoset resins of component (a) are selected from the group consisting of a thermoset acrylic melamine resin, an acrylic urethane resin, an epoxy carboxy resin, a silane modified acrylic melamine, an acrylic resin with carbamate pendant groups crosslinked with melamine or an acrylic polyol crosslinked with melamine containing carbamate groups.

The instant invention additionally pertains to a composition stabilized against degradation induced by heat, oxygen or light which comprises (a) a thermoplastic composition, and
(b) an effective stabilizing amount of a compound of formula 1,2,3,4,5 or 6 as defined above.

The thermoplastic resin of component (a) includes a polyolefin, polycarbonate, a styrenic, ABS, a polyamide (nylon), a polyester, a polyurethane, a polyacrylate, a polyimide, a rubber modified styrene resin, poly(vinyl chloride), poly(vinyl butyral), polyacetal (polyoxymethylene), or blends or copolymers such as poly (ethylene/1,4-cyclohexylenedimethylene terephthlate) PETG or an ethylene/acrylic acid copolymer or salt thereof (ionomer).

Still another embodiment of the thermoplastic resin is a polyester which is poly(ethylene terephthalate), poly(butylene terephthlate) or poly(ethylene 2,5-naphthalenedicarboxylate) PEN or a copolymer poly(ethylene/1,4-cyclohexylenedimethylene terephthlate) PETG.

Still another embodiment of the thermoplastic resin is a polyolefin which is polyethylene or polypropylene; or is polypropylene.

The thermoplastic resin of component (a) is a polyamide which is poly(m-phenylene isophthalamide), nylon 6 or nylon 66.

The thermoplastic resin of component (a) is a polyimide which is poly(p-phenylene pyromellitimide).

The instant invention additionally pertains to a composition stabilized against degradation induced by heat, oxygen or light which comprises (a) dyed or pigmented polypropylene, polyamide or polyester fibers, and (b) an effective stabilizing amount of a compound of formula 1,2,3,4,5 or 6 as defined above.

One embodiment of the invention is where the fibers of component (a) are pigmented polypropylene fibers.

It should be noted that candles contain a host of various components. The base materials may be made up of the following:

paraffin wax, natural oils, polyamide plus fatty acid/ester, fatty acids such as stearin, opacifiers, beeswax, glycerides plus oxidized wax, alcohols, and ethylene oligomers.

Candles also contain a number of additives such as the following:

mold release agents, fragrances, insect repellants or insecticides, hardeners, crystal modifiers, clarifiers, guttering reducers, colorants, f.p. control agents, stretchability improvers, gelling agents, extrusion aids, and vortex reducers.

Each of the various components are meant to control or modify the properties of the candle to insure proper burning, reduce channelling, aid in uniform melting, and the like. The colorants and fragrances obviously are there to provide the proper color, scent or other aesthetic appeal.

Of increasing importance are the transparent gel candles which look like clear glass, but which burn like a classical candle. As is discussed in detail in U.S. Pat. No. 5,879,694, the relevant parts of which are incorporated herein by reference, these gel candles usually contain a copolymer selected from the group consisting of a triblock, radial block, diblock or multiblock copolymer classically made up of at least two thermodynamically incompatible segments containing both hard and soft segments. Typical of such block copolymers is KRATON® (Shell Chemical Co.) which consists of block segments of styrene monomer units and rubber monomer or comonomer units. The most common structure found in KRATON® D series is a linear ABA block with styrene-butadiene-styrene (SBS) or styreneisoprene-styrene (SIS).

The following examples are meant for illustrative purposes only and are not to be construed to limit the instant invention in any manner whatsoever.

Raw Materials

Wax samples are supplied by the Candle-Lite Corporation. These samples contain dyes and fragrances.

The UV absorbers and hindered amine stabilizers are obtained from the Ciba Speciality Chemicals Corporation.

Sample Preparation

The wax samples obtained from the Candle-Lite Corporation already contain a dye and a fragrance (scent). In these cases, the wax is melted and the appropriate stabilizer(s) is (are) added and dissolved in the molten wax. The stabilized wax is then poured into five (5) 44 mm diameter aluminum pans giving five (5) wax disks.

Sample Exposure

Triplicate samples of each disk are exposed under a bank of six (6) cool-white fluorescent lamps (40 watts) or under a bank of six (6) UV lamps having a wavelength of 368 nm with the test samples being twelve (12) inches (30.48 cm) below the lamps.

Dye color fade (or color change) is measured by a Macbeth ColorEye Spectrophotometer with a 6 inch integrating sphere. The conditions are: 10 degree observer; D65 illuminant and 8 degree viewing angle.

Initial color measurements are taken using the above parameters. The L, a and b values are calculated using the CIE system from the reflectance values. YI is calculated from the L, a and b values. Subsequent measurements are taken at specified intervals. Delta L, a, b and YI values are simply the difference between the initial values and the values at each interval. Delta($\Delta$) E is calculated as follows:

$$[(\text{Delta } L)^2 + (\text{Delta } a)^2 + (\text{Delta } b)^2]^{1/2} = \text{Delta } E.$$

EXAMPLE 1

2,4-Bis[N-n-butyl—N—(1-cyclohexyloxy-2,2,6,6-tetramethylpiperidin-4-yl)amino]-6-[2-($C_{20}$–$C_{40}$alkanoyloxy)ethyl]amino-s-triazine 2,4-Bis[N-n-butyl—N—(1-cyclohexyloxy-2,2,6,6-tetramethylpiperidin-4-yl)amino]-6-(2-hydroxyethyl)amino-s-triazine (19.0 g, 0.025 mol), performacid 350 (12.0 g, 0.025 mol, Baker-Petrolite, $C_{20}$–$C_{40}$alkanoic acid), toluene (430 g, 4.67 mols), dicyclohexylcarbodiimide (5.5 g, 0.027 mol) and dimethylaminopyridine (0.4 g, 0.003 mol) are charged to a laboratory reactor. The reactor contents are heated to 95–100° C. and held there for six hours. The reaction mass is filtered hot through a small pad of silica gel. The solvent is removed by distillation and replaced with 300 mL of acetone. The resultant solution is filtered hot and the acetone is distilled off under reduced pressure. The title compound is obtained in a yield of 17.5 g, (58%) as a white solid melting with three melting point ranges 32–38° C.; 47° C. and 56° C. The structure is consistent with a mixture of esters of varying chain lengths and is confirmed by $^1$Hnmr and mass spectrometry.

EXAMPLE 2

1-Cyclohexyloxy-2,2,6,6-tetramethyl-4-$C_{20}$–$C_{40}$alkanoyloxypiperidine

1-Cyclohexyloxy-2,2,6,6-tetramethyl-4-hydroxypiperidine (12.8 g, 0.05 mol) and performacid 350

(24 g, 0.05 mol, $C_{20}$–$C_{40}$ alkanoic acid, Baker-Petrolite) are reacted together following the procedure of Example 1. The title compound is obtained in a yield of 9 g (25%) as a white solid with a melting point range of 35–41° C. The structure is consistent with a mixture of esters of varying chain lengths and is verified by $^1$Hnmr and mass spectrometry.

EXAMPLE 3

Color Fade of Pink Scented Candle Wax under UV Lamp Exposure

A variety of different stabilizers are evaluated in pink scented candle wax obtained from the Candle-Lite Corporation under UV lamp exposure. The ΔE values represent the change in color after the indicated days of exposure. A low ΔE value indicates less change in color and is highly desired.

| Sample* (wt % add) | ΔE after 32 days |
|---|---|
| Blank (no add) | 21.10 |
| A (0.3%) | 7.97 |
| D (0.3%) | 16.24 |
| B (0.15%) + C (0.15%) | 11.15 |
| A (0.15%) + E (0.15%) | 5.72 |
| A (0.15%) + E (0.3%) | 3.76 |

*A is octyl 3-(benzotriazol-2-yl)-5-tert-butyl-4-hydroxyhydrocinnamate, TINUVIN ® 384, CIBA.
B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
D is bis(1,2,2,6,6-pentamethylpiperidin-4-yl) sebacate, TINUVIN ® 292, CIBA.
E is 2,4-bis[N-n-butyl-N-(1-cyclohexyloxy-2,2,6,6-tetramethylpiperidin-4-yl)amino]-6-[2-($C_{20}$–$C_{40}$ alkanoyloxy)ethyl]amino-s-triazine, the compound of instant Example 1

These data show that the instant compound (Compound E) in combination with a UV absorber protects the pink scented candle wax from unwanted discoloration far better than conventional stabilizer systems.

EXAMPLE 4

Color Fade of Gray Scented Candle Wax under Fluorescent Lamp Exposure

A variety of different stabilizers are evaluated in gray scented candle wax obtained from the Candle-Lite Corporation under fluorescent lamp exposure. The ΔE values represent the change in color after the indicated days of exposure. A low ΔE value indicates less change in color and is highly desired.

| Sample* (wt % add) | ΔE after 29 days |
|---|---|
| Blank (no add) | 15.72 |
| A (0.3%) | 9.88 |
| B (0.15%) + C (0.15%) | 8.01 |
| A (0.15%) + E (0.15%) | 3.58 |
| A (0.15%) + F (0.15%) | 3.87 |
| G (0.15%) + E (0.15%) | 6.12 |
| G (0.15%) + F (0.15%) | 6.02 |
| G (0.15%) + F (0.3%) | 6.54 |

*A is octyl 3-(benzotriazol-2-yl)-5-tert-butyl-4-hydroxyhydrocinnamate, TINUVIN ® 384, CIBA.
B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
E is 2,4-bis[N-n-butyl-N-(1-cyclohexyloxy-2,2,6,6-tetramethylpiperidin-4-yl)amino]-6-[2-($C_{20}$–$C_{40}$ alkanoyloxy)ethyl]amino-s-triazine, the compound of instant Example 1.
F is 1-cyclohexyloxy-2,2,6,6-tetramethyl-4-$C_{20}$–$C_{40}$ alkanoyloxypiperidine, the compound of instant Example 2.
G is 2,4-bis(2,4-dimethylphenyl)-6-[2-hydroxy-4-(3-do-/tri-decyloxy-2-hydroxypropoxy)phenyl]-s-triazine, TINUVIN ® 400, CIBA.

These data show that an instant compound (Compound E or F) in combination with a UV absorber, particularly a benzotriazole UV absorber, protects the gray scented candle wax from unwanted discoloration far better than conventional stabilizer systems.

EXAMPLE 5

Color Fade of Gray Scented Candle Wax under UV Lamp Exposure

A variety of different stabilizers are evaluated in gray scented candle wax obtained from the Candle-Lite Corporation under fluorescent lamp exposure. The ΔE values represent the change in color after the indicated days of exposure. A low ΔE value indicates less change in color and is highly desired.

| Sample* (wt % add) | ΔE after 18 days |
|---|---|
| Blank (no add) | 29.97 |
| A (0.3%) | 8.82 |
| B (0.15%) + C (0.15%) | 10.21 |
| A (0.15%) + H (0.15%) | 5.04 |
| A (0.15%) + E (0.15%) | 4.29 |
| A (0.15%) + F (0.15%) | 4.76 |

*A is octyl 3-(benzotriazol-2-yl)-5-tert-butyl-4-hydroxyhydrocinnamate, TINUVIN ® 384, CIBA.
B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
E is 2,4-bis[N-n-butyl-N-(1-cyclohexyloxy-2,2,6,6-tetramethylpiperidin-4-yl)amino]-6-[2-($C_{20}$–$C_{40}$ alkanoyloxy)ethyl]amino-s-triazine, the compound of instant Example 1.
F is 1-cyclohexyloxy-2,2,6,6-tetramethyl-4-$C_{20}$–$C_{40}$ alkanoyloxypiperidine, the compound of instant Example 2.
H is bis(1-octyloxy-2,2,6,6-tetramethylpiperidin-4-yl) sebacate, TINUVIN ® 123, CIBA.

These data show that an instant compound (Compound E or F) in combination with a benzotriazole UV absorber protects the gray scented candle wax from unwanted discoloration far better than conventional stabilizer systems.

EXAMPLE 6

Color Fade of White Scented Candle Wax under Fluorescent Lamp Exposure

A variety of different stabilizers are evaluated in white scented candle wax obtained from the Candle-Lite Corporation under fluorescent lamp exposure. The ΔE values represent the change in color after the indicated days of exposure. A low ΔE value indicates less change in color and is highly desired.

| Sample* (wt % add) | ΔΔE after 24 days |
|---|---|
| Blank (no add) | 34.34 |
| D (0.3%) | 32.33 |
| A (0.3%) | 29.16 |
| B (0.15%) + C (0.15%) | 20.08 |
| A (0.15%) + D (0.15%) | 31.06 |
| A (0.15%) + F (0.15%) | 15.33 |
| G (0.15%) + E (0.15%) | 12.82 |
| G (0.15%) + F (0.15%) | 16.82 |
| G (0.15%) + F (0.3%) | 12.96 |
| A (0.15%) + E (0.15%) | 10.99 |
| A (0.15%) + E (0.3%) | 7.29 |

*A is octyl 3-(benzotriazol-2-yl)-5-tert-butyl-4-hydroxyhydrocinnamate, TINUVIN ® 384, CIBA.
B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
D is bis(1,2,2,6,6-pentamethylpiperidin-4-yl) sebacate, TINUVIN ® 292, CIBA.
E is 2,4-bis[N-n-butyl-N-(1-cyclohexyloxy-2,2,6,6-tetramethylpiperidin-4-yl)amino]-6-[2-($C_{20}$–$C_{40}$ alkanoyloxy)ethyl]amino-s-triazine, the compound of instant Example 1.
F is 1-cyclohexyloxy-2,2,6,6-tetramethyl-4-$C_{20}$–$C_{40}$ alkanoyloxypiperidine, the compound of instant Example 2.
G is 2,4-bis(2,4-dimethylphenyl)-6-[2-hydroxy-4-(3-do-/tri-decyloxy-2-hydroxypropoxy)phenyl]-s-triazine, TINUVIN ® 400, CIBA.

These data show that an instant compound (Compound E or F) in combination with a UV absorber, particularly a benzotriazole UV absorber, protects the white scented candle wax from unwanted discoloration far better than conventional stabilizer systems.

EXAMPLE 7

Color Fade of White Scented Candle Wax under UV Lamp Exposure

A variety of different stabilizers are evaluated in white scented candle wax obtained from the Candle-Lite Corporation under UV lamp exposure. The ΔE values represent the change in color after the indicated days of exposure. A low ΔE value indicates less change in color and is highly desired.

| Sample* (wt % add) | ΔE after 25 days |
|---|---|
| Blank (no add) | 45.09 |
| D (0.3%) | 32.03 |
| A (0.3%) | 25.50 |
| B (0.15%) + C (0.15%) | 30.11 |
| A (0.15%) + D (0.15%) | 29.74 |
| G (0.15%) + E (0.15%) | 24.89 |
| A (0.15%) + F (0.15%) | 20.14 |
| A (0.15%) + E (0.15%) | 17.13 |
| A (0.15%) + E (0.3%) | 14.66 |

*A is octyl 3-(benzotriazol-2-yl)-5-tert-butyl-4-hydroxyhydrocinnamate, TINUVIN ® 384, CIBA.
B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
D is bis(1,2,2,6,6-pentamethylpiperidin-4-yl) sebacate, TINUVIN ® 292, CIBA.
E is 2,4-bis[N-n-butyl-N-(1-cyclohexyloxy-2,2,6,6-tetramethylpiperidin-4-yl)amino]-6-[2-($C_{20}$–$C_{40}$ alkanoyloxy)ethyl]amino-s-triazine, the compound of instant Example 1.
F is 1-cyclohexyloxy-2,2,6,6-tetramethyl-4-$C_{20}$–$C_{40}$ alkanoyloxypiperidine, the compound of instant Example 2.
G is 2,4-bis(2,4-dimethylphenyl)-6-[2-hydroxy-4-(3-do-/tri-decyloxy-2-hydroxypropoxy)phenyl]-s-triazine, TINUVIN ® 400, CIBA.

These data show that an instant compound (Compound E or F) in combination with a UV absorber, particularly a benzotriazole UV absorber, protects the white scented candle wax from unwanted discoloration far better than conventional stabilizer systems.

EXAMPLE 8

Thermal Permanence of the Instant Compounds

The instant compounds are subjected to thermogravimetric analysis to measure their thermal permanence relative to the commercial hindered amine stabilizer, TINUVIN® 770.

| Compound | Temperature ° C. at 10% wt loss | Temperature ° C. at 50% wt loss |
|---|---|---|
| TINUVIN ® 770* | 255 | 297 |
| Example 1 | 284 | 368 |

*TINUVIN ° 770 is bis(2,2,6,6-tetramethylpiperidin-4yl) sebacate, CIBA.

These data show the improved thermal permanence of the instant compounds compared to the commerical hindered amine stabilizer TINUVIN® 770.

EXAMPLE 9

Preparation of LDPE Films for HALS Migration Values

Ground low density polyethylene powder (Dow 640 I) is tumble blended with the desired quantity of test long chain hindered amine (HALS) and 0.30% by weight of Superfloss antiblock agent. The blended resin is twin-screw compounded at 450° F. (232° C.). The resulting pellets are blown at 400° F. (204° C.) into a monolayer film of approximately 3 mil thickness.

Blown films are used to study the migration of the test HALS from the interior of the film to the film surface. Additives that migrate tend to produce a white deposit on the film surface which can be easily scraped off. This is the phenomenon called blooming. It is clear that, if the additive blooms on to the surface of the film and is easily removed therefrom, it cannot serve to protect the film itself which is its purpose.

Visual assessment of the film surface is performed at approximately 30 day intervals up to 375 days. The films are stored at room temperature.

The instant long chain hindered amine compounds are particularly effective in LDPE films in the prevention of blooming because of their non-migration properties.

EXAMPLE 10

PET Bottles

Poly(ethylene terephthalate), PET, concentrates (10% by weight) of the instant long chain hindered amine compounds are prepared using Eastapak 9921W PET, on a 27 mm twin screw extruder at an operating temperature at the die of 275° C. The concentrates are let down with base resin to the final additives loading of 0.3% by weight based on resin. PET is dried under vacuum for at least four hours at 240° F. prior to preform molding. Preforms are molded on a unit cavity Arburg press using the minimum injection temperature and back pressure necessary to obtain parts free of haze and crystallinity. Bottle blow molding is conducted using a Sidel SBO 2/3 blow molding machine, using preforms described above. Bottle wall thickness of 0.015–0.016 inches is achieved.

The instant compounds are particular eficacious because of their ability to protect the resin from unwanted degradation and without migration into the bottle contents.

EXAMPLE 11

To separate poly(ethylene terephthalate), PET, resin formulations containing 0.5% by weight of the instant long chain hindered amine are added 0.5% by weight of each of the following benzotriazole stabilizers:

(a) 5-chloro-2-(2-hydroxy-3-α-cumyl-5-tert-octylphenyl)-2H-benzotriazole;

(b) isooctyl 3-(5-chloro-2H-benzotriazol-2-yl)-5-tert-butyl-4-hydroxyhydrocinnamate;

(c) 2-(2-hydroxy-3-α-cumyl-5-tert-octylphenyl)-2H-benzotriazole;

(d) 5-trifluoromethyl-2-(2-hydroxy-3-α-cumyl-5-tert-octylphenyl)-2H-benzotriazole;

(e) 5-butylsulfonyl-2-(2-hydroxy-3-α-cumyl-5-tert-octylphenyl)-2H-benzotriazole;

(f) 5-trifluoromethyl-2-(2-hydroxy-3-α-cumyl-5-tert-butylphenyl)-2H-benzotriazole;

(g) 5-trifluoromethyl-2-(2-hydroxy-5-tert-octylphenyl)-2H-benzotriazole;

(h) 5-trifluoromethyl-2-(2-hydroxy-3,5-di-tert-octylphenyl)-2H-benzotriazole;

(i) 5-trifluoromethyl-2-(2-hydroxy-3,5-di-tert-butylphenyl)-2H-benzotriazole;

(j) 5-trifluoromethyl-2-(2-hydroxy-3,5-di-α-cumylphenyl)-2H-benzotriazole;

(k) 5-butylsulfonyl-2-(2-hydroxy-3,5-di-tert-butylphenyl)-2H-benzotriazole;

(l) 5-phenylsulfonyl-2-(2-hydroxy-3,5-di-tert-butylphenyl)-2H-benzotriazole; or (m) methyl 3-(5-trifluoromethyl-2H-benzotriazol-2-yl)-5-tert-butyl-4-hydroxyhydrocinnamate.

Each of the stabilized resin compositions are then blow or injection molded into a PET bottle having incorporated therein each of the respective UV absorbers. The PET bottles are especially effective at protecting the contents therein from UV radiation allowing for a longer shelf like for the product contained in the bottle.

EXAMPLE 12

To separate poly(ethylene terephthalate), PET, resin formulations containing 0.5% by weight of the instant long chain hindered amine are added 0.5% by weight of each of the following benzotriazole stabilizers:

(i) 2,4-bis(4-biphenylyl)-6-(2-hydroxy-4-octyloxycarbonylethyideneoxyphenyl)-s-triazine;

(ii) 2-phenyl-4[2-hydroxy-4-(3-sec-butyloxy-2-hydroxypropyloxy)phenyl]-6-[2-hydroxy-4-(3-sec-amyloxy-2-hydroxypropyloxy)phenyl]-s-triazine;

(iii) 2,4-bis(2,4-dimethylphenyl)-6-[2-hydroxy-4-(3-benzyloxy-2-hydroxypropyloxy)-phenyl]-s-triazine; (3-sec-amyloxy-2-hydroxypropyloxy)phenyl]-s-triazine;

(iv) 2,4-bis(2-bydroxy-4-n-butyloxyphenyl)-6-(2,4-di-n-butyloxyphenyl)-s-triazine;

(v) 2,4-bis(2,4-dimethylphenyl)-6-[2-hydroxy-4-(3-nonyloxy*-2-hydroxypropyloxy)-5-α-cumylphenyl]-s-triazine; (*denotes a mixture of oxtyloxy, nonyloxy and decyloxy groups)

(vi) methylenebis-[2.4-bis(2,4-dimethylphenyl)-6-[2-hydroxy-4-(3-butyloxy-2-hydroxy-propoxy)phenyl]-s-triazine, methylene bridged dimer mixture bridged in the 3:5',5:5' and 3:3' positions in a 5:4:1 ratio;

(vii) 2,4,6-tris(2-hydroxy-4-isooctyloxycarbonylisopropylideneoxyphenyl)-s-triazine;

(viii) 2,4-bis(2,4-dimethylphenyl)-6-(2-hydroxy-4-hexyloxy-5-α-cumylphenyl)-s-triazine;

(ix) 2,4-bis(2,4-dimethylphenyl)-6-(2-hydroxy-4-octyloxy-phenyl)-s-triazine; CYASORB® 1164, Cytec;

(x) 2-(2,4,6-trimethylphenyl)-4,6-bis[2-hydroxy-4-(3-butyloxy-2-hydroxypropyloxy)-phenyl]-s-triazine; or (xi) 2,4,6-tris[2-hydroxy-4-(3-sec-butyloxy-2-hydroxypropyloxy)phenyl]-s-triazine.

Each of the stabilized resin compositions are then blow or injection molded into a PET bottle having incorporated therein each of the respective UV absorbers. The PET bottles are especially effective at protecting the contents therein from UV radiation allowing for a longer shelf like for the product contained in the bottle.

EXAMPLE 13

A multi-layer bottle is prepared wherein the exterior layer and the innermost layer contacting the bottle contents are composed of PET and which also comprises a barrier layer. When one or more of the benzotriazoles or s-triazine UV absorbers listed in Examples 11 and 12 and an instant long chain hindered amine are incorporated into any of the three layers at 0.5% by weight based on the weight of the resin, the contents of the bottle are effectively protected from UV radiation.

EXAMPLE 14

A multi-layer bottle is prepared wherein the exterior layer and the innermost layer contacting the bottle contents are composed of HDPE (high density polyethylene) and which also comprises a barrier layer.When one or more of the benzotriazoles or s-triazine UV absorbers listed in Examples 11 and 12 and an instant long chain hindered amine are incorporated into any of the three layers at 0.5% by weight based on the weight of the resin, the contents of the bottle are effectively protected from UV radiation.

EXAMPLE 15

A multi-layer bottle is prepared wherein the exterior layer and the innermost layer contacting the bottle contents are composed of polypropylene and which also comprises a barrier layer. When one or more of the benzotriazoles or s-triazine UV absorbers listed in Examples 11 and 12 and an instant long chain hindered amine are incorporated into any of the layers at 0.5% by weight based on the weight of the resin, the contents of the bottle are effectively protected from UV radiation.

The compounds listed under Examples 16 to 46 are prepared following the general procedures found in Examples 1 and 2 and in the U.S. Pat. Nos. 5,204,473; 5,216,156; 5,844,026 and 6,166,212.

EXAMPLES 16–24

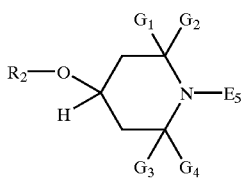

(1)

| Ex* | $E_5$ | $E_9$ | E** | $R_2$** | $T_1$ | |
|---|---|---|---|---|---|---|
| 16 | $OE_9$ | methyl | — | —$COT_1$ | $C_{40}$–$C_{60}$ | — |
| 17 | $OE_9$ | octyl | — | —$COT_1$ | $C_{20}$–$C_{40}$ | — |
| 18 | $OE_9$ | benzyl | — | —$COT_1$ | $C_{80}$–$C_{100}$ | — |
| 19 | $OE_9$ | cyclo-hexenyl | — | A | $C_{20}$–$C_{40}$ | m is 4; X is —O— |
| 20* | $OE_9$ | octa-decyl | — | B | $C_{80}$–$C_{100}$ | p is 10; X is $NCH_3$ |
| 21 | $OE(OH)_b$ | — | C | —$COT_1$ | $C_{20}$–$C_{40}$ | b is 1 |
| 22* | $OE(OH)_b$ | — | D | —$COT_1$ | $C_{60}$–$C_{80}$ | b is 2 |
| 23 | $OE(OH)_b$ | — | C | —$COXT_1$ | $C_{20}$–$C_{40}$ | b is 1 |
| 24 | $OE(OH)_b$ | — | C | —$COT_1$ | $C_{40}$–$C_{60}$ | b is 1 |

*Unless otherwise noted, $G_1$ to $G_4$ are each methyl.
In Example 20, $G_1$ and $G_3$ are each methyl, and $G_2$ and $G_4$ are each ethyl.
In Example 22, $G_1$ to $G_4$ are n-propyl.
**A is —$(CH_2)_m$CO—X—$T_1$.
B is —$(CH_2)_p$—X—CO—$T_1$.
C is —$CH_2C(CH_3)_2$—OH.
D is —$CH_2CH(OH)$—$CH_2OH$.

EXAMPLES 25–32

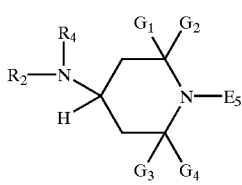

(2)

| Ex* | $E_5$ | $E_9$ | E** | $R_2$** | $T_1$ | |
|---|---|---|---|---|---|---|
| 25 | $OE_9$ | methyl | — | —$COT_1$ | $C_{20}$–$C_{40}$ | $R_4$ is $CH_3$ |
| 26 | $OE_9$ | cyclo-hexyl | — | —$COT_1$ | $C_{40}$–$C_{60}$ | $R_4$ is H |
| 27 | $OE_9$ | octyl | — | —$COT_1$ | $C_{80}$–$C_{100}$ | $R_4 = C_4H_9$ |
| 28 | $OE_9$ | phenyl | — | E | $C_{20}$–$C_{40}$ | m is 6; X is —O—; $R_4$ is H |
| 29* | $OE(OH)_b$ | — | C | —$COT_1$ | $C_{20}$–$C_{40}$ | $R_4$ is $CH_3$; b is 1 |

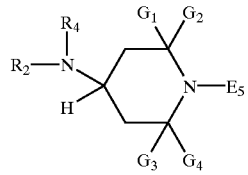

(2)

| Ex* | $E_5$ | $E_9$ | E** | $R_2$** | $T_1$ | |
|---|---|---|---|---|---|---|
| 30* | $OE(OH)_b$ | — | D | $T_1$ | $C_{40}$–$C_{60}$ | b is 2; $R_4$ is H |
| 31 | $OE(OH)_b$ | — | C | A | $C_{20}$–$C_{40}$ | b is 1; $R_4$ is H; p is 3 |
| 32 | $OE(OH)_b$ | — | C | F | $C_{20}$–$C_{40}$ | b is 1; $R_4$ is $CH_3$; p is 6 |

*Unless otherwise noted, $G_1$ to $G_4$ are each methyl.
In Example 30, $G_1$ and $G_3$ are each octyl, and $G_2$ and $G_4$ are each methyl.
**A is —$(CH_2)_m$CO—X—$T_1$.
C is —$CH_2C(CH_3)_2$—OH.
D is —$CH_2CH(OH)$—$CH_2OH$.
E is —$(CH_2)_m$—CO—$T_1$.
F is —CO—$(CH_2)_p$—X—CO—$T_1$.

EXAMPLES 33–40

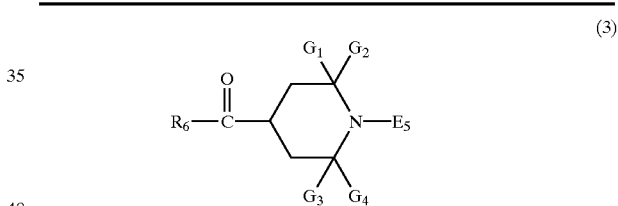

(3)

| Ex* | $E_5$ | $E_9$ | E** | $R_6$** | $T_1$ | |
|---|---|---|---|---|---|---|
| 33 | $OE_9$ | methyl | — | —$XT_1$ | $C_{20}$–$C_{40}$ | X is —O— |
| 34 | $OE_9$ | cyclo-hexyl | — | —$XT_1$ | $C_{40}$–$C_{80}$ | X is —O— |
| 35 | $OE_9$ | octyl | — | —$XT_1$ | $C_{20}$–$C_{40}$ | X is —NH— |
| 36 | $OE_9$ | phenyl | — | G | $C_{20}$–$C_{40}$ | m is 6; X is —O—; $X_1$ is —O— |
| 37 | $OE_9$ | allyl | — | —$XT_1$ | $C_{20}$–$C_{40}$ | X is —O— |
| 38 | $OE(OH)_b$ | — | C | —$XT_1$ | $C_{20}$–$C_{40}$ | b is 1 |
| 39 | $OE(OH)_b$ | — | C | —$XT_1$ | $C_{20}$–$C_{40}$ | b is 1; X is $NCH_3$ |
| 40 | $OE(OH)_b$ | — | H | I | $C_{20}$–$C_{40}$ | b is 2; p is 3; X is NCH3; $X_1$ is —O— |

*Unless otherwise noted, $G_1$ to $G_4$ are each methyl.
**
C is —$CH_2C(CH_3)_2$—OH.
G is —X—$(CH_2)_m$—CO—$X_1$—$T_1$.
H is —$CH_2$—$CH(OH)$—$CH_2CH_2OH$.
I is —X—$(CH_2)_p$—$X_1$—CO—$T_1$.

EXAMPLES 41–46

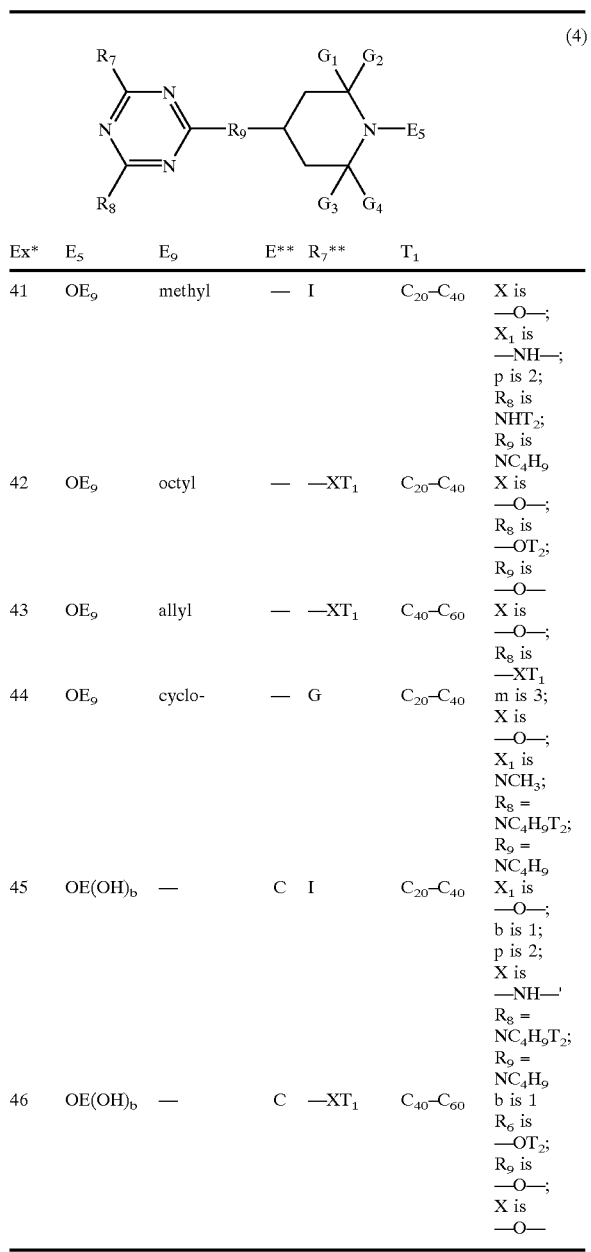

| Ex* | $E_5$ | $E_9$ | E | $R_7$ | $T_1$ | |
|---|---|---|---|---|---|---|
| 41 | $OE_9$ | methyl | — | I | $C_{20}$–$C_{40}$ | X is —O—; $X_1$ is —NH—; p is 2; $R_8$ is $NHT_2$; $R_9$ is $NC_4H_9$ |
| 42 | $OE_9$ | octyl | — | —$XT_1$ | $C_{20}$–$C_{40}$ | X is —O—; $R_8$ is —$OT_2$; $R_9$ is —O— |
| 43 | $OE_9$ | allyl | — | —$XT_1$ | $C_{40}$–$C_{60}$ | X is —O—; $R_8$ is —$XT_1$ |
| 44 | $OE_9$ | cyclo- | — | G | $C_{20}$–$C_{40}$ | m is 3; X is —O—; $X_1$ is $NCH_3$; $R_8$ = $NC_4H_9T_2$; $R_9$ = $NC_4H_9$ |
| 45 | $OE(OH)_b$ | — | C | I | $C_{20}$–$C_{40}$ | $X_1$ is —O—; b is 1; p is 2; X is —NH—' $R_8$ = $NC_4H_9T_2$; $R_9$ = $NC_4H_9$ |
| 46 | $OE(OH)_b$ | — | C | —$XT_1$ | $C_{40}$–$C_{60}$ | b is 1 $R_6$ is —$OT_2$; $R_9$ is —O—; X is —O— |

*Unless otherwise noted, $G_1$ to $G_4$ are each methyl.
**
C is $CH_2C(CH_3)_2$—OH.
G is —X—$(CH_2)_m$—CO—$X_1$—$T_1$.
I is —X—$(CH_2)_p$—$X_1$—CO—$T_1$.

What is claimed is:
1. A compound of formula 4, 5 or 6

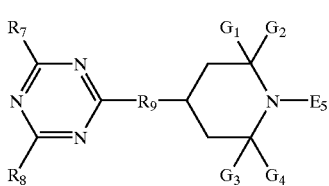

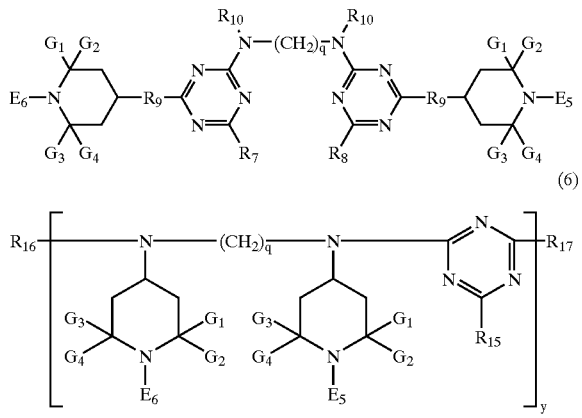

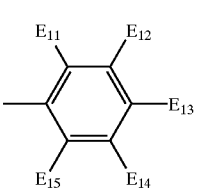

where
- $G_1$, $G_2$, $G_3$, and $G_4$ are independently alkyl of 1 to 8 carbon atoms, or $G_1$ and $G_2$ together are pentamethylene, or $G_3$ and $G_4$ together are pentamethylene;
- $E_5$ is $OE_9$ or —O—E—$(OH)_b$;
- $E_9$ is straight or branched chain alkyl of 1 to 24 carbon atoms, cycloalkyl of 5 to 12 carbon atoms, straight or branched chain alkenyl of 3 to 24 carbon atoms, cycloalkenyl of 5 to 12 carbon atoms, phenylalkyl of 7 to 15 carbon atoms, a radical of a saturated or unsaturated bicyclic or tricyclic hydrocarbon of 7 to 15 carbon atoms, aryl of 6 to 10 carbon atoms or said aryl substituted by one to three alkyl of 1 to 4 carbon atoms; or a group of formula IV (IV)

[structure with $E_{11}$, $E_{12}$, $E_{13}$, $E_{14}$, $E_{15}$ on benzene ring]

- $E_{11}$ to $E_{15}$ are independently hydrogen, halogen, nitro, cyano, alkyl of 1 to 18 carbon atoms, phenylalkyl of 7 to 15 carbon atoms, aryl of 6 to 10 carbon atoms, hydroxyl, carboxyl, alkylthio of 1 to 18 carbon atoms, alkoxy or 1 to 18 carbon atoms, phenylalkoxy of 7 to 15 carbon atoms, aryloxy of 6 to 10 carbon atoms, alkylcarbonyloxy of 2 to 18 carbon atoms, alkylsulfonyl of 1 to 18 carbon atoms, arylsulfonyl of 6 to 15 carbon atoms, sulfo or phosphono, or any two vicinal substituents connected together to form a mono- or polycyclic ring;
- E is a straight or branched chain alkylene of 1 to 18 carbon atoms, cycloalkylene of 5 to 18 carbon atoms, cycloalkenylene of 5 to 18 carbon atoms, a straight or branched chain alkylene of 1 to 4 carbon atoms substituted by phenyl or by phenyl substituted by one or two alkyl groups of 1 to 4 carbon atoms;
- b is 1, 2 or 3 with the proviso that b cannot exceed the number of carbon atoms in E, and when b is 2 or 3, each hydroxyl group is attached to a different carbon atom of E;
- $R_7$ and $R_8$ are independently chlorine, alkoxy of 1 to 18 carbon atoms, —O—$T_2$, amino substituted by 2-hydroxyethyl, —NH(alkyl) of 1 to 18 carbon atoms, —N(alkyl)T$_2$ with alkyl of 1 to 18 carbon atoms, —N(alkyl)$_2$ of 2 to 36 carbon atoms, —X—T$_1$, X—(CH$_2$)$_m$—CO—X$_1$—T$_1$, or X—(CH$_2$)$_p$—X$_1$—CO—T$_1$;

T$_1$ is straight or branched chain alkyl of 19 to 100 carbon atoms, or said alkyl substituted by one hydroxyl group and interrupted by one oxa moiety, or a mixture of such alkyl moieties; or T$_1$ is —(R—O)$_n$—R—OG$_5$ where R is ethylene, propylene, trimethylene, 1,2-butylene or tetramethylene, and n is 4 to 49 so that the total number of carbon atoms in T$_1$ is at least 20;

G$_5$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms;

X and X$_1$ are independently —O—, or —N—(R$_4$)—;

R$_4$ is hydrogen, alkyl of 1 to 18 carbon atoms or acyl of 2 to 6 carbon atoms;

m is 1 to 12;

p is 1 to 12;

R$_9$ is a divalent oxygen atom, or R$_9$ is a divalent nitrogen atom substituted by either hydrogen, alkyl of 1 to 12 carbon atoms or T$_2$

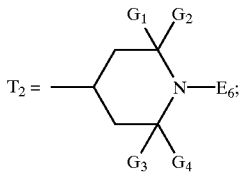

E$_6$ is hydrogen, oxyl, hydroxyl, straight or branched chain alkyl of 1 to 24 carbon atoms, straight or branched chain alkenyl of 3 to 24 carbon atoms, benzyl, acetyl, —CH$_2$CH(OH)—E$_8$, —OE$_9$, or, —OE(OH)$_b$;

E$_8$ is hydrogen, methyl, ethyl or phenyl;

R$_{10}$ is hydrogen or an alkyl group of 1 to 18 carbon atoms;

q is 2 to 8;

y is 1 to 10;

R$_{15}$ is morpholino, piperidino, 1-piperizinyl, alkylamino of 1 to 18 carbon atoms, especially branched alkylamino of 3 to 8 carbon atoms such as tert-octylamino, —N(alkyl)T$_2$ with alkyl of 1 to 8 carbon atoms, —N(alkyl)$_2$ of 2 to 16 carbon atoms, —X—T$_1$, X—(CH$_2$)$_m$13 CO—X$_1$—T$_1$, or X—(CH$_2$)$_p$—X$_1$—CO—T$_1$;

R$_{16}$ is hydrogen, acyl of 2 to 4 carbon atoms, carbamoyl substituted by alkyl of 1 to 4 carbon atoms, s-triazinyl substituted once by chlorine and once by R$_{15}$, or s-triazinyl substituted twice by R$_{15}$ with the condition that the two R$_{15}$ substituents may be different;

R$_{17}$ is chlorine, amino substituted by alkyl of 1 to 18 carbon atoms or by T$_2$, —N(alkyl)T$_2$ with alkyl of 1 to 8 carbon atoms, —N(alkyl)$_2$ of 2 to 16 carbon atoms, or the group T$_3$

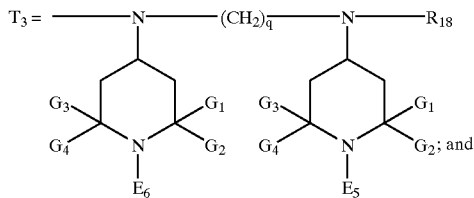

R$_{18}$ is hydrogen, acyl of 2 to 4 carbon atoms, carbamoyl substituted by alkyl of 1 to 4 carbon atoms, s-triazinyl substituted twice by —N(alkyl)$_2$ of 2 to 16 carbon atoms or s-triazinyl substituted twice by —N(alkyl)T$_1$ with alkyl of 1 to 8 carbon atoms;

with the proviso that at least one of R$_7$, R$_8$, or R$_{15}$ is a group which contains a T$_1$ moiety.

2. A compound according to claim 1 of formula 4

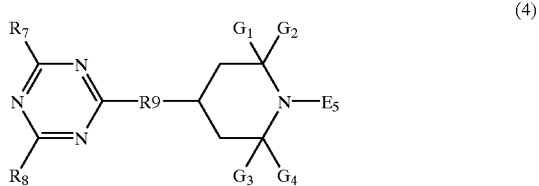

(4)

G$_1$, G$_2$, G$_3$, and G$_4$ are each methyl;

E$_5$ is OE$_9$ or —O—E—(OH)$_b$;

E$_9$ is straight or branched chain alkyl of 1 to 24 carbon atoms, cycloalkyl of 5 to 12 carbon atoms, straight or branched chain alkenyl of 3 to 24 carbon atoms, or cycloalkenyl of 5 to 12 carbon atoms; or a group of formula IV

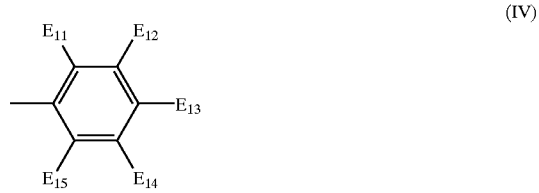

(IV)

E$_{11}$ to E$_{15}$ are independently hydrogen, F, Cl, Br, nitro, cyano, hydroxyl, carboxyl, alkylthio of 1 to 18 carbon atoms, alkoxy or 1 to 18 carbon atoms;

when b is 1, E—OH is respectively a carbon-centered radical formed from 2-methyl-2-propanol, 2-propanol, 2,2-dimethyl-1-propanol, 2-methyl-2-butanol, ethanol, 1-propanol, 1-butanol, 1-pentanol, 1-hexanol, 1-nonanol, 1-decanol, 1-dodecanol, 1-octadecanol, 2-butanol, 2-pentanol, 2-ethyl-1-hexanol, cyclohexanol, cyclooctanol, allyl alcohol, phenethyl alcohol or 1-phenyl-1-ethanol;

when b is 2, E—OH is respectively a carbon-centered radical or diradical formed from 1,2-ethanediol, 1,2-propanediol, 1,3-propanediol, 1,2-butanediol, 1,3-butanediol, 1,4-butanediol, 2,2-dimethyl-1,3-propanediol, 1,2-cyclohexanediol, 1,3-cyclohexanediol or 1,4-cyclohexanediol;

when b is 3, E—OH is respectively a carbon-centered radical formed from glycerol, 1,1,1-tris(hydroxymethyl)methane, 2-ethyl-2-hydroxymethyl-1,3-propanediol, 1,2,4-butanetriol or 1,2,6-hexanetriol;

m is 1 to 4;

p is 1 to 4;

$T_1$ is straight or branched chain alkyl of 19 to 80 carbon atoms, or a mixture of such alkyl moieties; or $T_1$ is —(R—O)$_n$—R—OG$_5$ where R is ethylene, or propylene and n is 4 to 49 so that the total number of carbon atoms in $T_1$ is at least 20;

$G_5$ is hydrogen, straight or branched chain alkyl of 1 to 24 carbon atoms;

X and $X_1$ are independently —O—, or —N—($R_4$)—;

$R_4$ is hydrogen, alkyl of 1 to 18 carbon atoms or acyl of 2 to 6 carbon atoms;

$R_7$ and $R_8$ are independently alkoxy of 1 to 18 carbon atoms, —O—$T_2$, amino substituted by 2-hydroxyethyl, —N(alkyl)$T_2$ with alkyl of 1 to 18 carbon atoms, —X—$T_1$, X—(CH$_2$)$_m$—CO—$X_1$—$T_1$, or X—(CH$_2$)$_p$—$X_1$—CO—$T_1$;

$R_9$ is a divalent oxygen atom, or $R_9$ is a divalent nitrogen atom substituted by either hydrogen, alkyl of 1 to 12 carbon atoms or $T_2$

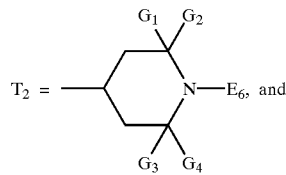

$E_6$ is hydrogen, hydroxyl, straight or branched chain alkyl of 1 to 24 carbon atoms, straight or branched chain alkenyl of 3 to 24 carbon atoms, benzyl, acetyl, —OE$_9$, or —OE(OH)$_b$.

3. A compound according to claim 1 of formula 5

(5)

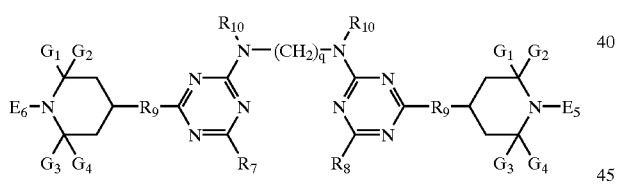

$G_1$, $G_2$, $G_3$, and $G_4$ are each methyl;

$E_5$ is OE$_9$ or —O—E—(OH)$_b$;

$E_9$ is straight or branched chain alkyl of 1 to 24 carbon atoms, cycloalkyl of 5 to 12 carbon atoms, straight or branched chain alkenyl of 3 to 24 carbon atoms, or cycloalkenyl of 5 to 12 carbon atoms; or a group of formula IV (IV)

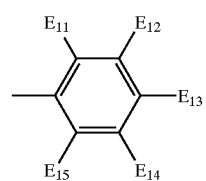

$E_{11}$ to $E_{15}$ are independently hydrogen, F, Cl, Br, nitro, cyano, hydroxyl, carboxyl, alkylthio of 1 to 18 carbon atoms, or alkoxy or 1 to 18 carbon atoms;

when b is 1, E—OH is respectively a carbon-centered radical formed from 2-methyl-2-propanol, 2-propanol, 2,2-dimethyl-1-propanol, 2-methyl-2-butanol, ethanol, 1-propanol, 1-butanol, 1-pentanol, 1-hexanol, 1-nonanol, 1-decanol, 1-dodecanol, 1-octadecanol, 2-butanol, 2-pentanol, 2-ethyl-1-hexanol, cyclohexanol, cyclooctanol, allyl alcohol, phenethyl alcohol or 1-phenyl-1-ethanol;

when b is 2, E—OH is respectively a carbon-centered radical or diradical formed from 1,2-ethanediol, 1,2-propanediol, 1,3-propanediol, 1,2-butanediol, 1,3-butanediol, 1,4-butanediol, 2,2-dimethyl-1,3-propanediol, 1,2-cyclohexanediol, 1,3-cyclohexanediol or 1,4-cyclohexanediol;

when b is 3, E—OH is respectively a carbon-centered radical formed from glycerol, 1,1,1-tris (hydroxymethyl)methane, 2-ethyl-2-hydroxymethyl-1,3-propanediol, 1,2,4-butanetriol or 1,2,6-hexanetriol;

m is 1 to 4;

p is 1 to 4;

$T_1$ is straight or branched chain alkyl of 19 to 80 carbon atoms or a mixture of such alkyl moieties; or $T_1$ is —(R—O)$_n$—R—OG$_5$ where R is ethylene or propylene and n is 4 to 49 so that the total number of carbon atoms in $T_1$ is at least 20;

$G_5$ is hydrogen, straight or branched chain alkyl of 1 to 24 carbon atoms;

X and $X_1$ are independently —O—, or —N—($R_4$)—;

$R_4$ is hydrogen, alkyl of 1 to 18 carbon atoms;

$R_7$ and $R_8$ are independently alkoxy of 1 to 18 carbon atoms, —O—$T_2$, amino substituted by 2-hydroxyethyl, —NH(alkyl) of 1 to 18 carbon atoms, —N(alkyl)$T_2$ with alkyl of 1 to 18 carbon atoms, —X—$T_1$, X—(CH$_2$)$_m$—CO—$X_1$—$T_1$, or X—(CH$_2$)$_p$—$X_1$—CO—$T_1$;

$R_9$ is a divalent oxygen atom, or $R_9$ is a divalent nitrogen atom substituted by either hydrogen, alkyl of 1 to 12 carbon atoms or $T_2$

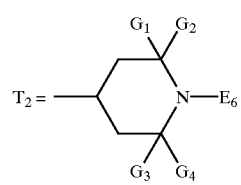

$E_6$ is hydrogen, oxyl, hydroxyl, straight or branched chain alkyl of 1 to 24 carbon atoms, straight or branched chain alkenyl of 3 to 24 carbon atoms, acetyl, —OE$_9$, or, —OE(OH)$_b$;

$R_{10}$ is hydrogen or an alkyl group of 1 to 18 carbon atoms, and q is 4 to 8.

4. A compound according to claim 1 of formula 6

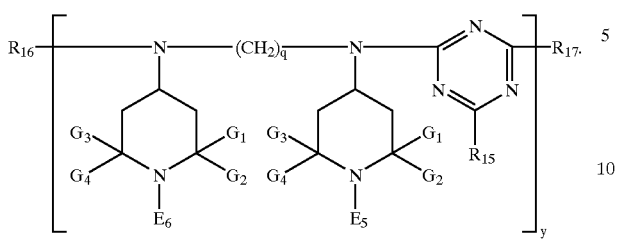

(6)

$G_1$, $G_2$, $G_3$, and $G_4$ are each methyl;

$E_5$ is $OE_9$ or —O—E—(OH)$_b$;

$E_9$ is straight or branched chain alkyl of 1 to 24 carbon atoms, cycloalkyl of 5 to 12 carbon atoms, straight or branched chain alkenyl of 3 to 24 carbon atoms, or cycloalkenyl of 5 to 12 carbon atoms; or a group of formula IV

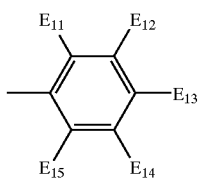

(IV)

$E_{11}$ to $E_{15}$ are independently hydrogen, F, Cl, Br, nitro, cyano, hydroxyl, carboxyl, alkylthio of 1 to 18 carbon atoms, or alkoxy or 1 to 18 carbon atoms;

when b is 1, E—OH is respectively a carbon-centered radical formed from 2-methyl-2-propanol, 2-propanol, 2,2-dimethyl-1-propanol, 2-methyl-2-butanol, ethanol, 1-propanol, 1-butanol, 1-pentanol, 1-hexanol, 1-nonanol, 1-decanol, 1-dodecanol, 1-octadecanol, 2-butanol, 2-pentanol, 2-ethyl-1-hexanol, cyclohexanol, cyclooctanol, allyl alcohol, phenethyl alcohol or 1-phenyl-1-ethanol;

when b is 2, E—OH is respectively a carbon-centered radical or diradical formed from 1,2-ethanediol, 1,2-propanediol, 1,3-propanediol, 1,2-butanediol, 1,3-butanediol, 1,4-butanediol, 2,2-dimethyl-1,3-propanediol, 1,2-cyclohexanediol, 1,3-cyclohexanediol or 1,4-cyclohexanediol;

when b is 3, E—OH is respectively a carbon-centered radical formed from glycerol, 1,1,1-tris(hydroxymethyl)methane, 2-ethyl-2-hydroxymethyl-1,3-propanediol, 1,2,4-butanetriol or 1,2,6-hexanetriol;

m is 1 to 4;

p is 1 to 4;

$T_1$ is straight or branched chain alkyl of 19 to 80 carbon atoms or a mixture of such alkyl moieties; or $T_1$ is —(R—O)$_n$—R—OG$_5$ where R is ethylene or propylene and n is 4 to 49 so that the total number of carbon atoms in $T_1$ is at least 20;

$G_5$ is hydrogen, straight or branched chain alkyl of 1 to 24 carbon atoms;

X and $X_1$ are independently —O—, or —N—(R$_4$)—;

$R_4$ is hydrogen, alkyl of 1 to 18 carbon atoms;

$R_7$ and $R_8$ are independently alkoxy of 1 to 18 carbon atoms, —O—$T_2$, amino substituted by 2-hydroxyethyl, —NH(alkyl) of 1 to 18 carbon atoms, —N(alkyl)$T_2$ with alkyl of 1 to 18 carbon atoms, —X—$T_1$, X—(CH$_2$)$_m$—CO—$X_1$—$T_1$, or X—(CH$_2$)$_p$—$X_1$—CO—$T_1$;

$R_9$ is a divalent oxygen atom, or $R_9$ is a divalent nitrogen atom substituted by either hydrogen, alkyl of 1 to 12 carbon atoms or $T_2$

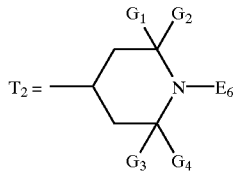

$E_6$ is hydrogen, oxyl, hydroxyl, straight or branched chain alkyl of 1 to 24 carbon atoms, straight or branched chain alkenyl of 3 to 24 carbon atoms, acetyl, —OE$_9$, or, —OE(OH)$_b$;

$R_{10}$ is hydrogen or an alkyl group of 1 to 18 carbon atoms, q is 4 to 8;

y is 1 to 10;

$R_{15}$ is morpholino, piperidino, 1-piperizinyl, alkylamino of 1 to 8 carbon atoms, especially branched alkylamino of 3 to 8 carbon atoms such as tert-octylamino, —X—$T_1$, X—(CH$_2$)$_m$—CO—$X_1$—$T_1$, or X—(CH$_2$)$_p$—$X_1$—CO—$T_1$;

$R_{16}$ is hydrogen, acyl of 2 to 4 carbon atoms, carbamoyl substituted by alkyl of 1 to 4 carbon atoms, s-triazinyl substituted once by chlorine and once by $R_{15}$;

$R_{17}$ is amino substituted by alkyl of 1 to 18 carbon atoms or by $T_2$, —N(alkyl)$T_2$ with alkyl of 1 to 8 carbon atoms, —N(alkyl)$_2$ of 2 to 16 carbon atoms, or the group $T_3$

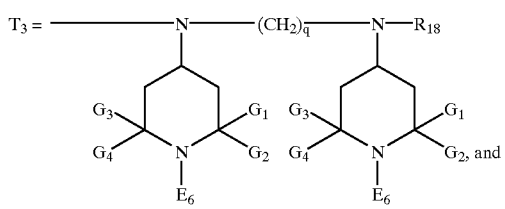

$R_{18}$ is hydrogen.

5. A compound according to claim 1 of formula 4

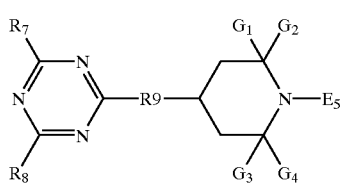

(4)

$G_1$, $G_2$, $G_3$, and $G_4$ are each methyl;

$E_5$ is $OE_9$ or —O—E—(OH)$_b$;

$E_9$ is straight or branched chain alkyl of 1 to 12 carbon atoms, or cycloalkyl of 5 to 10 carbon atoms, b is 1;

when b is 1, E—OH is respectively a carbon-centered radical formed from 2-methyl-2-propanol;

$T_1$ is straight or branched chain alkyl of 19 to 60 carbon atoms, or a mixture of such alkyl moieties; or X and $X_1$ are independently —O—, or —N—$(R_4)$—;

$R_4$ is hydrogen or methyl;

$R_7$ and $R_8$ are independently —O—$T_2$, —N(alkyl)$T_2$ with alkyl of 1 to 18 carbon atoms, —X—$T_1$, or X—$(CH_2)_p$—$X_1$—CO—$T_1$;

$R_9$ is a divalent oxygen atom, or $R_9$ is a divalent nitrogen atom substituted by either hydrogen, alkyl of 1 to 12 carbon atoms or $T_2$

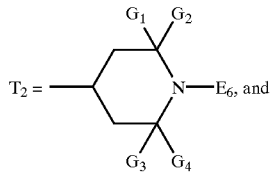

$E_6$ is hydrogen, hydroxyl, straight or branched chain alkyl of 1 to 12 carbon atoms, acetyl, —$OE_9$, or —$OE(OH)_b$.

6. A compound according to claim 1 which is (a) 2,4-bis[N-n-butyl-N-(1-cyclohexyloxy-2,2,6,6-tetramethylpiperidin-4-yl)amino]-6-[2-($C_{20}$–$C_{40}$alkanoyloxy)ethyl]amino-s-triazine;

(l) 2,4-bis[N-n-butyl-N-(1-methoxy-2,2,6,6-tetramethylpiperidin-4-yl)amino]-6-[2-($C_{20}$–$C_{40}$alkanoyloxy)ethyl]amino-s-triazine;

(m) 2,4-bis(1-octyloxy-2,2,6,6-tramethylpiperidin-4-yloxy)-6-($C_{20}$–$C_{40}$alkyloxy)-s-triazine;

(o) 2,4-bis{(N-n-butyl-N-[1-(2-methyl-2-hydroxypropyloxy)-2,2,6,6-tramethylpiperidin-4yl]amino}-6-[2-($C_{20}$–$C_{40}$alkanoyloxy)ethyl]amino-s-triazine; or (p) 2,4-bis[1-(2-methyl-2-hydroxypropyloxy)-2,2,6,6-tetramethylpiperidin-4-yloxy)-6-($C_{40}$–$C_{60}$alkyloxy)-s-triazine.

7. A compound according to claim 6 which is (a) 2,4-bis[N-n-butyl-N-—(1-cyclohexyloxy-2,2,6,6-tramethylpiperidin-4-yl)amino]-6-[2-($C_{20}$–$C_{40}$alkanoyloxy)ethyl]amino-s-triazine.

* * * * *